US012600989B2

(12) United States Patent
Wang

(10) Patent No.: US 12,600,989 B2
(45) Date of Patent: Apr. 14, 2026

(54) ADENO-ASSOCIATED VIRUS (AAV) VECTOR AND USES THEREFOR

(71) Applicant: The Trustees of the University of Pennsylvania, Philadelphia, PA (US)

(72) Inventor: Qiang Wang, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 552 days.

(21) Appl. No.: 18/248,967

(22) PCT Filed: Oct. 18, 2021

(86) PCT No.: PCT/US2021/055436
§ 371 (c)(1),
(2) Date: Apr. 13, 2023

(87) PCT Pub. No.: WO2022/082109
PCT Pub. Date: Apr. 21, 2022

(65) Prior Publication Data
US 2023/0383313 A1      Nov. 30, 2023

Related U.S. Application Data

(60) Provisional application No. 63/093,275, filed on Oct. 18, 2020.

(51) Int. Cl.
*C12N 15/86*          (2006.01)

(52) U.S. Cl.
CPC .... *C12N 15/86* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| | | | |
|---|---|---|---|
| 5,139,941 | A | 8/1992 | Muzyczka et al. |
| 5,741,683 | A | 4/1998 | Zhou et al. |
| 6,057,152 | A | 5/2000 | Samulski et al. |
| 6,200,560 | B1 | 3/2001 | Couto et al. |
| 6,204,059 | B1 | 3/2001 | Samulski et al. |
| 6,221,349 | B1 | 4/2001 | Couto et al. |
| 6,268,213 | B1 | 7/2001 | Samulski et al. |
| 6,491,907 | B1 | 12/2002 | Rabinowitz et al. |
| 6,596,535 | B1 | 7/2003 | Carter |
| 6,660,514 | B1 | 12/2003 | Zolotukhin et al. |
| 6,951,753 | B2 | 10/2005 | Shenk et al. |
| 7,094,604 | B2 | 8/2006 | Snyder et al. |
| 7,125,717 | B2 | 10/2006 | Carter |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,439,065 | B2 | 10/2008 | Ferrari et al. |
| 7,442,373 | B2 | 10/2008 | Morrow et al. |
| 7,456,683 | B2 | 11/2008 | Takano et al. |
| 7,588,772 | B2 | 9/2009 | Kay et al. |

| | | | |
|---|---|---|---|
| 7,906,111 | B2 | 3/2011 | Wilson et al. |
| 10,265,417 | B2 | 4/2019 | Wilson et al. |
| 10,485,883 | B2 | 11/2019 | Wilson et al. |
| 10,695,441 | B2 | 6/2020 | Wilson et al. |
| 10,973,928 | B2 | 4/2021 | Wilson et al. |
| 11,357,867 | B2 | 6/2022 | Wilson et al. |
| 11,357,868 | B2 | 6/2022 | Wilson et al. |
| 2013/0045186 | A1 | 2/2013 | Gao et al. |
| 2018/0243416 | A1* | 8/2018 | Limberis .............. A61K 39/145 |
| 2020/0056159 | A1 | 2/2020 | Wilson et al. |
| 2020/0155704 | A1 | 5/2020 | Wilson et al. |

FOREIGN PATENT DOCUMENTS

| | | |
|---|---|---|
| WO | WO-2003/042397 | 5/2003 |
| WO | WO-2005/033321 | 4/2005 |
| WO | WO-2006/110689 | 10/2006 |
| WO | WO-2011/126808 | 10/2011 |
| WO | WO-2013/049493 | 4/2013 |
| WO | WO-2017/075119 | 5/2017 |
| WO | WO-2017/160360 | 9/2017 |
| WO | WO-2018/022608 | 2/2018 |
| WO | WO-2018/160582 | 9/2018 |
| WO | WO-2019/168961 | 9/2019 |
| WO | WO-2019/169004 | 9/2019 |
| WO | WO-2019/241535 | 12/2019 |
| WO | WO-2020/132455 | 6/2020 |
| WO | WO-2021/158915 | 8/2021 |
| WO | WO-2021/165537 | 8/2021 |

OTHER PUBLICATIONS

Buller et al., "Characterization of adenovirus-associated virus-induced polypeptides in KB cells," J. Virol., Jan. 1978, vol. 25:331-338.

Buning et al., "Recent developments in adeno-associated virus vector technology," J. Gene Med., May 2008, vol. 10:717-733.

Calcedo et al., "Worldwide Epidemiology of Neutralizing Antibodies to Adeno-Associated Viruses," Journal of Infectious Diseases, Feb. 2009, vol. 199(3)381-390.

Carter, "Handbook of Parvoviruses", Tijsser (ed.), CRC Press, Jan. 1990, pp. 155-168.

Clement et al., "Manufacturing of recombinant adeno-associated viral vectors for clinical trials," Mol Ther Methods Clin Dev, Mar. 2016, vol. 3:16002.

Fisher et al., "Transduction with Recombinant Adeno-Associated Virus for Gene Therapy is Limited by Leading-Strand Synthesis," J. Virol., Jan. 1996, vol. 70:520-532.

(Continued)

*Primary Examiner* — Tracy Vivlemore
*Assistant Examiner* — Fatimah Khalaf Matalkah
(74) *Attorney, Agent, or Firm* — Howson & Howson LLP; Cathy A. Kodroff

(57) ABSTRACT

Provided herein are engineered nucleic acid sequences encoding AAVhu68 which provide improved yields of packaged AAVhu68 viral particles. Also provided is a packaging host cell comprising the engineered nucleotide sequence and methods of using same to product recombinant AAVhu68 vectors useful for gene delivery. Further provided are production cell supernatants comprising improved yields of recombinant AAV vectors having AAVhu68 capsids produced using the nucleotide sequences provided herein.

18 Claims, 12 Drawing Sheets

Specification includes a Sequence Listing.

(56)            References Cited

OTHER PUBLICATIONS

Gao et al., "Adeno-associated viruses undergo substantial evolution in primates during natural infections," PNAS, May 2003, vol. 100(10):6081-6086.

Gao et al., "Clades of Adeno-Associated Viruses are Widely Disseminated in Human Tissues," J Virol, Jun. 2004, vol. 78(12):6381-6388.

Green and Sambrook (eds.), Molecular Cloning: A Laboratory Manual, Cold Spring Harbor Press, Jan. 2012, 2 pages, Cold Spring Harbor, NY.

Grieger & Samulski, "Adeno-associated virus as a gene therapy vector: Vector development, production and clinical applications," Adv. Biochem. Engin/Biotechnol., Oct. 2005, vol. 99: 119-145.

Grimm et al., "Titration of AAV-2 particles via a novel capsid ELISA: packaging of genomes can limit production of recombinant AAV-2," Gene therapy, Mar. 1999, vol. 6(7):1322-1330.

Lock et al., "Absolute Determination of Single-Stranded and Self-Complementary Adeno-Associated Viral Vector Genome Titers by Droplet Digital PCR," Human Gene Therapy, Apr. 2014, vol. 25:115-125.

Lock et al., "Rapid, Simple, and Versatile Manufacturing of Recombinant Adeno-Associated Viral Vectors at Scale, " Human Gene Therapy, Oct. 2010, vol. 21:1259-127.

McCarty et al., "Self-complementary recombinant adeno-associated virus (scAAV) vectors promote efficient transduction independently of DNA synthesis," Gene Therapy, Aug. 2001, vol. 8(16):1248-1254.

Nei et al., "Neighbor Joining (NJI) Method," Molecular Evolution and Phylogenetics, Jan. 2000, pp. 103-110, Oxford University Press, New York.

Povlich et al., "Particle Titer Determination and Characterization of rAAV Molecules Using Nanoparticle Tracking Analysis," Molecular Therapy: AAV Vectors II, May 2016, vol. 24(S1):S122.

Rayaprolu et al., "Comparative Analysis of Adeno-Associated Virus Capsid Stability and Dynamics," J Virol., Dec. 2013, vol. 87(24): 13150-13160.

Rose et al., "Structural proteins of adenovirus-associated viruses," J. Virol., Nov. 1971, vol. 8:766-770.

Sambrook et al., "Molecular Cloning. A Laboratory Manual (2nd Ed.)," Jan. 1989, 2 pgs, Cold Spring Harbor Laboratory, New York.

Sawada-Hirai et al., "Human anti-anthrax protective antigen neutralizing monoclonal antibodies derived from donors vaccinated with anthrax vaccine adsorbed," J Immune Based Ther, Vaccines, May 2004, vol. 2:1-15.

Sofronescu, "Cerebrospinal Fluid Analysis," Jun. 2022, 11 pages, accessed Sep. 13, 2023 at emedicine.medscape.com/article/2093316-overview.

Sommer et al., "Quantification of Adeno-Associated Virus Particles and Empty Capsids by Optical Density Measurement," Molec. Ther., Jan. 2003, vol. 7:122-128.

Thomson et al., "A comprehensive comparison of multiple sequence alignments", Nucl. Acids. Res., Jul. 1999, vol. 27(13):2682-2690.

UniProtKB, "P51608—MECP2_Human," Oct. 1996, 10 pages, accessed Jul. 6, 2023 from https://www.uniprot.org/uniprotk/P51608/entry.

Wu et al., "Optimization of self-complementary AAV vectors for liver-directed expression results in sustained correction of hemophilia B at low vector dose," Molecular therapy: The Journal of the American Society of Gene Therapy, Dec. 2007, vol. 16(2).

Zanta-Boussif et al., "Validation of a mutated PRE sequence allowing high and sustained transgene expression while abrogating WHV-X protein synthesis: application to the gene therapy of WAS," Gene Therapy, Mar. 2009, vol. 16: 605-619.

International Search Report and Written Opinion issued on International Patent Application No. PCT/US2021/055436, dated Feb. 23, 2022.

U.S. Appl. No. 63/002,100, filed Mar. 30, 2020.

U.S. Appl. No. 63/027,731, filed May 20, 2020.

U.S. Appl. No. 63/023,593, filed May 12, 2020.

U.S. Appl. No. 63/043,562, filed Jun. 24, 2020.

U.S. Appl. No. 63/069,651, filed Aug. 24, 2020.

U.S. Appl. No. 63/079,290, filed Sep. 16, 2020.

U.S. Appl. No. 63/093,275, filed Oct. 18, 2020.

U.S. Appl. No. 63/038,488, filed Jun. 12, 2020.

* cited by examiner

FIG 1A

```
AAVhu68_eng   atggctgccgatggttatcttccagattggctcgaggacaacctcagtgaaggcattcgc   60
AAVhu68       atggctgccgatggttatcttccagattggctcgaggacaacctcagtgaaggcattcgc   60
              ************************************************************

AAVhu68_eng   gagtggtggctttgaaacctggagccccctcaaccaagcaaatcaacaacatcaagac   120
AAVhu68       gagtggtggctttgaaacctggagccccctcaaccaagcaaatcaacaacatcaagac   120
              ********************************************************

AAVhu68_eng   aacgctcggggtcttgtgcttccgggttacaaataccttggacccggcaacggactcgac   180
AAVhu68       aacgctcggggtcttgtgcttccgggttacaaataccttggacccggcaacggactcgac   180
              ************************************************************

AAVhu68_eng   aagggggagccggtcaacgaagcagagacgcggccctcgagcacgacaaggcctacgac   240
AAVhu68       aagggggagccggtcaacgaagcagagacgcggccctcgagcacgacaaggcctacgac   240
              **********************************************************

AAVhu68_eng   cagcagctcaaggccggagacaaccgtacctcaagtacaaccacgccgacgccgagttc   300
AAVhu68       cagcagctcaaggccggagacaaccgtacctcaagtacaaccacgccgacgccgagttc   300
              **********************************************************

AAVhu68_eng   caggagcggctcaaagaagagatacgtctttttgggggcaacctcggggcgagcagtcttccag   360
AAVhu68       caggagcggctcaaagaagagatacgtctttttgggggcaacctcggggcgagcagtcttccag   360
              ******************************************************

AAVhu68_eng   gccaaaaagaggcttcttgaacctcttggtctggtttgaggaagcggctaagacggctcct   420
AAVhu68       gccaaaaagaggcttcttgaacctcttggtctggtttgaggaagcggctaagacggctcct   420
              ************************************************************
```

FIG 1B

```
AAVhu68_eng  ggaaagaagaggcctgtagagcagtctcctcaggaaccggactcctccgtgggtattggc  480
AAVhu68      ggaaagaagaggcctgtagagcagtctcctcaggaaccggactcctccgtgggtattggc  480
             ************************************************************

AAVhu68_eng  aaatcgggtgcacagcccgctaaaaagagactcaatttcggtcagactggcgacacagag  540
AAVhu68      aaatcgggtgcacagcccgctaaaaagagactcaatttcggtcagactggcgacacagag  540
             ************************************************************

AAVhu68_eng  tcagtccccgaccctcaaccaatcggagaacctcccgcagcccctcagtgtgggatct   600
AAVhu68      tcagtccccgaccctcaaccaatcggagaacctcccgcagcccctcagtgtgggatct   600
             ************************************************************

AAVhu68_eng  cttacaatggcttcaggtggtggcgcaccagtggcagacaataacgaaggtgccgatgga  660
AAVhu68      cttacaatggcttcaggtggtggcgcaccagtggcagacaataacgaaggtgccgatgga  660
             ************************************************************

AAVhu68_eng  gtgggtagttcctcgggaaattggcattgcgattcccaatggctgggggacagagtcatc  720
AAVhu68      gtgggtagttcctcgggaaattggcattgcgattcccaatggctgggggacagagtcatc  720
             ************************************************************

AAVhu68_eng  accaccagcaccgaacctgggccctgcccactacaacaatcacctctacaagcaaaatc   780
AAVhu68      accaccagcaccgaacctgggccctgcccactacaacaatcacctctacaagcaaaatc   780
             ************************************************************

AAVhu68_eng  tccaacagcacatctggaggatcttcaaatgacaacgcctacttcggctacagcaccccc  840
AAVhu68      tccaacagcacatctggaggatcttcaaatgacaacgcctacttcggctacagcaccccc  840
             ************************************************************
```

FIG 1C

AAVhu68_eng    tggggtattttgacttcaaacagattccactgccacttctcaccacgtgactggcaaaga    900
AAVhu68        tggggtattttgacttcaaacagattccactgccacttctcaccacgtgactggcaaaga    900
               ************************************************************

AAVhu68_eng    ctcatcaacaacactggggattccggcctaagcgactcaacttcaagctcttcaacatt    960
AAVhu68        ctcatcaacaacactggggattccggcctaagcgactcaacttcaagctcttcaacatt    960
               ***********************************************************

AAVhu68_eng    caggtcaaagaggttacggacaacaatggagtcaagaccatcgctaataaccttaccagc    1020
AAVhu68        caggtcaaagaggttacggacaacaatggagtcaagaccatcgctaataaccttaccagc    1020
               ************************************************************

AAVhu68_eng    acggtccagtctcttcacggactcagactatcagctcccgtacgtgctcggtcggctcac    1080
AAVhu68        acggtccagtctcttcacggactcagactatcagctcccgtacgtgctcggtcggctcac    1080
               ************************************************************

AAVhu68_eng    gagggctgcctcccgccgttcccagcggacgtttcatgattcctcagtatggatacctc    1140
AAVhu68        gagggctgcctcccgccgttcccagcggacgtttcatgattcctcagtatacgggtatcta    1140
               *********************************************  . .  .

AAVhu68_eng    accctgaacgacggcagtcaggcggtgggccgctcatcctctctactgcctggtacttc    1200
AAVhu68        acgcttaatgatggaagccaagccgtgggtcgttcgtccttactgcctgtcctgaatatttc    1200
               *   * * .* .* *   **  . * * *..  ***

AAVhu68_eng    ccttcgcagatgctgaggactggcaacaacttccagttcagctacgagttcgagaacgtc    1260
AAVhu68        ccgtcgcaaatgctaagaacgcgggtaacaacttccagttcagctacgagttgagaacgta    1260
                * .*** .*.**.*.   **************** ****. .

FIG 1D

```
AAVhu68_eng  cctttccacagcagctacgcccacagccagccagagtttggaccgcttgatgaaccctctgatc  1320
AAVhu68      cctttccatagcagctatgtcacagccaaagcctggactcacgaatccactcatc          1320
             ******** ****** *** ****** **  *******  **.** **:** ***

AAVhu68_eng  gaccagtacctgtactacctgtcaaagacgatcaaacggttctggccagaaccagcagacg    1380
AAVhu68      gaccaatacttgtactatctctcaaagactattaacggttctggacagaatcaacaaacg    1380
             *****.**** ******** *** ****** **  ****** ***.** .***

AAVhu68_eng  ctgaagttcagcgtggccggcctagcaacatggccgtccagggcagaaactacatccct     1440
AAVhu68      ctaaaattcagtgtggccggacccagcaacatggctgtccagggaagaaactacatacct    1440
             **.** **** ********* .** ********** ********* .*********.***

AAVhu68_eng  gggcccagctaccggcagcagagagtctcaaccactgactcagaacaacaacagtgag      1500
AAVhu68      ggaccagctaccggacacaacgtgtctcaaccactgactcaaaacaacaacagcgaa      1500
             ** .***** ******** .** .*:*********** ******* .***** ** .

AAVhu68_eng  ttcgcctggcctggcgccagctctcttgggccctcaacggccgcaactgctgatgaacccca  1560
AAVhu68      tttgcttggcctggagcttctcttcttgggctctcaatggacgtaatagcttgatgaatcct  1560
             ** *** ****** ** ******  ***** ****** **.** .* ******* **:

AAVhu68_eng  ggcccagccagtcacaaggagggcgaggacccgtttctccctttgtctggctct         1620
AAVhu68      ggacctgctatggccagccacaaagaaggagaggaccgttctcttccttgtctggatct    1620
             **.* .*:** *** ****** **** .*.** ** ****** *******.***

AAVhu68_eng  ctgatcttcggcaagcagcagggacccggcagagacagcaacgtggacgcgcgacaagtcatgatc  1680
AAVhu68      ttaattttttggcaaaacaaggaacaactgaaagagagacaacgggatgcgcggacaaagtcatgata  1680
             *.** ** ** *********** **.** :**.*** *** .* ******* .*.******
```

FIG 1E

```
AAVhu68_eng  acgaacgagaggaggagatcaagaccaccaacccctgtggcaaccgagtcctacggccaggtg  1740
AAVhu68      accaacgaagaagaagaaattaaaaactaccaacccagtagcaacccagtagcaacggagtcctatggcaagtg  1740
             ** * ***..*.** .*.** ****** .:**.* ******* ** .**.***

AAVhu68_eng  gcaaccaaccaccagagcgcccaggcgcccaggcgccagactgctggtccagaaccagggg  1800
AAVhu68      gccacacaaccaccagagtgcccaagtgcccaagcgccgacgcgcgggttcaaaaccaagga  1800
             *. .* .************ ***** .*.*.*****.* ** .**.***.**.

AAVhu68_eng  atcctgcctggcatggtgtgtggcaggaccgtgacgtgtacctgcaggggccctatctgggca  1860
AAVhu68      atacttccgggtatgttggcaggacagagatgtgtacctgcaggggccattgggcc  1860
             **.** ** ***********.********.:.*.**.* ****** .

AAVhu68_eng  aagatccctcacacggacggcaacttccaccctctctcctgatggcggcttcggcatg  1920
AAVhu68      aaaattcctcacacggacggcaacttcaccccttctccgctgatggaggtttgggaatg  1920
             ** .** ****************** .**.** **.*.** ** .***

AAVhu68_eng  aagcaccccgcctcctcagatcctctcagatcctctcagatcctcatcaagaacactccggtccccggcagacccctccgacg  1980
AAVhu68      aagcaccccgcctcctcagatcctctcagatcctcatcaaacacaccgtacctgcggatcctccaacg  1980
             ***********************************.**:.* ** .*. .** *** .***

AAVhu68_eng  gccttcaacaaggacaagctgaactcattcattcactcagtactccactggccaggtcagc  2040
AAVhu68      gctttcaacaaggacaagctgaactctttcatcaccccagtattctactggccaagtcagc  2040
             ** ****************** ** .** *** .**.* ** ** .** **.

AAVhu68_eng  gtggagatcgagtgtgggagctgcagaaggagaacagcaagcgttggaacccagagatccag  2100
AAVhu68      gtggagattgagtgtgggagctgcagaaggaaaaacagcaagcgctggaacccggagatccag  2100
             ******** **************************.***********.
```

FIG 1F

```
AAVhu68_eng   tacacttccaactactacaagtctaacaacgtggagttcgccgtcaacactgagggtgtg   2160
AAVhu68       tacacttccaactattacaagtctaataatgttgaatttgctgttaatactgaaggtgtt   2160
              *************** ******** *.* ** ** ***** ***** .******

AAVhu68_eng   tacagtgagcctcgccctatcggcaccggtacctcacccgaaacttgtga   2211
AAVhu68       tattctgaaccccgccccattggcaccagataccctgactcgtaatctgtaa   2211
              ** .; .***.** ****** ** ****** ..******* *** ** **;** *** . *
```

AAVhu68_eng

AAVhu68

AAV2 Rep

Cap

KanR p5256 (pAAV2 hu68M191 KanR)
8030 bp

ADENO-ASSOCIATED VIRUS (AAV) VECTOR AND USES THEREFOR

CROSS-REFERENCE TO RELATED APPLICATIONS

This is a National Stage Entry under 35 U.S.C. 371 of International Patent Application No. PCT/US2021/055436, filed Oct. 18, 2021, which claims the benefit of U.S. provisional patent application No. 63/093,275, filed Oct. 18, 2020. These applications are incorporated by reference herein.

BACKGROUND OF THE INVENTION

Adeno-associated virus (AAV), a member of the Parvovirus family, is a small non-enveloped, icosahedral virus with single-stranded linear DNA (ssDNA) genomes of about 4.7 kilobases (kb) long. The wild-type genome comprises inverted terminal repeats (ITRs) at both ends of the DNA strand, and two open reading frames (ORFs): rep and cap. Rep is composed of four overlapping genes encoding rep proteins required for the AAV life cycle, and cap contains overlapping nucleotide sequences of capsid proteins: VP1, VP2 and VP3, which self-assemble to form a capsid of an icosahedral symmetry.

The use of replication-defective, recombinant AAV as a delivery vehicle for gene therapy applications have been described, as AAV is not associated with any known clinical sequelae. Multiple different AAV clades have been identified [G. Gao, et al, PNAS, May 13, 2003, 100(10) 6081-6086] and differences have emerged in the tissues which each of the different clades target, as well as differences with the clade. [G Gao et al, J Virol, 78(12): 2004 June: 6381-6388]. Vectors having capsids in clade F, e.g., AAV9 and AAVhu68, have been described as being useful for targeting central nervous system (CNS) and cardiac cells. The AAVhu68 capsid was isolated from human tissue and was found to have two amino acid differences from the previously described the human AAV9 capsid sequence. See, WO 2018/160582.

As the gene therapy field expands, the need for production systems capable of generating large amounts of recombinant AAV particles is a hurdle to be overcome.

SUMMARY OF THE INVENTION

Novel AAVhu68 capsid coding sequences are described, which are useful in manufacturing of recombinant AAV (rAAV) for generating higher yields of recombinant AAV having AAVhu68 capsids. Plasmids for delivery of nucleic acid molecules to host cells and host cells comprising the novel capsid coding sequences are provided herein. In certain embodiments, a nucleic acid molecule is provided which comprises a nucleic acid sequence of SEQ ID NO: 1 or a nucleic acid sequence at least 95%, at least 97%, or at least 99% identical to SEQ ID NO:1, which encodes the AAVhu68 VP1 amino acid sequence of SEQ ID NO: 2.

In certain embodiments, a recombinant adeno-associated virus (rAAV) production system useful for producing a recombinant AAVhu68 virus is provided. The production system comprises: (a) the AAVhu68 capsid coding nucleic acid sequence of SEQ ID NO: 1 or a sequence at least 99% identical thereto; (b) a nucleic acid molecule suitable for packaging into the AAVhu68 capsid, said nucleic acid molecule comprising at least one AAV inverted terminal repeat (ITR) and a non-AAV nucleic acid sequence encoding a gene product operably linked to sequences which direct expression of the product in a host cell; and (c) sufficient AAV rep functions and helper functions to permit packaging of the nucleic certain embodiments, the AAV rep is AAVhu68rep characterized by the amino acid sequence of SEQ ID NO: 6, or a functional fragment thereof. In certain embodiments, the AAV rep is encoded by the nucleic acid sequence of SEQ ID NO: 5.

In certain embodiments, a suspension comprising production host cells is provided acid molecule into the recombinant AAVhu68 capsid. In certain embodiments, the nucleic acid sequence of (a) comprises at least SEQ ID NO: 1, or a sequence at least 99% identical to SEQ ID NO: 1 which encodes the amino acid sequence of SEQ ID NO: 2. In certain embodiments, the system further comprises the nucleic acid sequence of about nucleotide (nt) 607 to about nt 2211 of SEQ ID NO: 1 encoding the AAVhu68 vp3 of about aa 203 to about amino acid 736 of SEQ ID NO: 2.

In certain embodiments, a production host cell for generating a recombinant adeno-associated virus (rAAV) having an AAVhu68 capsid is provided which comprises: (a) a nucleic acid sequence encoding the AAVhu68 VP1 capsid protein having the nucleotide sequence of SEQ ID NO: 1 or a sequence at least 99% identical thereto operably linked to expression control sequences which direct expression of AAVhu68 capsid protein in the host cell; (b) a nucleic acid molecule for packaging into the AAVhu68 capsid, said nucleic acid molecule comprising AAV inverted terminal repeat (ITR) sequences flanking the extreme 5' and 3' end, respectively, of a non-AAV nucleic acid sequence encoding a gene product operably linked to sequences which direct expression of the product in a host cell; and (c) sufficient AAV rep functions and helper functions to permit packaging of the nucleic acid molecule into the AAVhu68 capsid. Optionally, the host cell further comprises a nucleic acid sequence of about nucleotide (nt) 607 to about nt 2211 of SEQ ID NO: 1 or a sequence at least 99% identical thereto encoding the AAVhu68 vp3 of about amino acid 203 to about amino acid 736 of SEQ ID NO: 2.

In certain embodiments, the helper functions are provided by adenovirus, baculovirus, or herpes simplex virus proteins. The AAV rep may be from a different AAV than AAVhu68, e.g., AAV2. In certain embodiments, the AAV rep coding sequence and cap genes are on the same nucleic acid molecule, wherein there is optionally a spacer between the rep sequence and cap gene. In certain embodiments, the spacer is SEQ ID NO: 9. In herein containing the novel AAVhu68 coding sequence. In certain embodiments, the helper functions are herpes simplex virus helper functions. In other embodiments, the helper functions are baculovirus helper functions. In certain embodiments, a cell culture comprises production host cells as described herein containing the novel AAVhu68 coding sequence.

In certain embodiments, the helper functions are adenovirus helper functions. In certain embodiments, a surface or substrate is provided having an adherent production host cell containing the novel AAVhu68 coding sequence. In certain embodiments, a culture is provided which comprises production host cells.

The production system, suspension, or cell culture described herein expressing AAVhu68 from the engineered coding sequence afford an increased yield of rAAVhu68 particles as compared to the native AAVhu68 coding sequence. In certain embodiments, the yield is at least 20% higher than the yield with the AAVhu68 coding sequence provided in SEQ ID NO: 3. In certain embodiments, the yield is at least 30% higher than the yield with the AAVhu68 coding sequence provided in SEQ ID NO: 3.

In certain embodiments, a composition is provided which comprises a mixed population of recombinant adeno-associated virus hu68 (rAAVhu68) produced using the engineered AAVhu68 coding sequence.

In still a further aspect, a method for increasing yield and/or packaging efficiency of a recombinant adeno-associated (rAAV) vector is provided.

In still a further embodiment, an engineered rAAV produced according to this method is provided.

Still other advantages of the invention will be apparent from the following detailed description of the invention.

BRIEF DESCRIPTION OF THE DRAWINGS

FIGS. 1A-1F show an alignment of the engineered AAVhu68M191 (AAVhu68_eng) nucleic acid sequence [SEQ ID NO: 1] encoding the vp1 capsid protein of AAVhu68 [SEQ ID NO: 2] with the previously published AAVhu68 nucleic acid sequence [SEQ ID NO: 3].

DETAILED DESCRIPTION OF THE INVENTION

Figure 2:
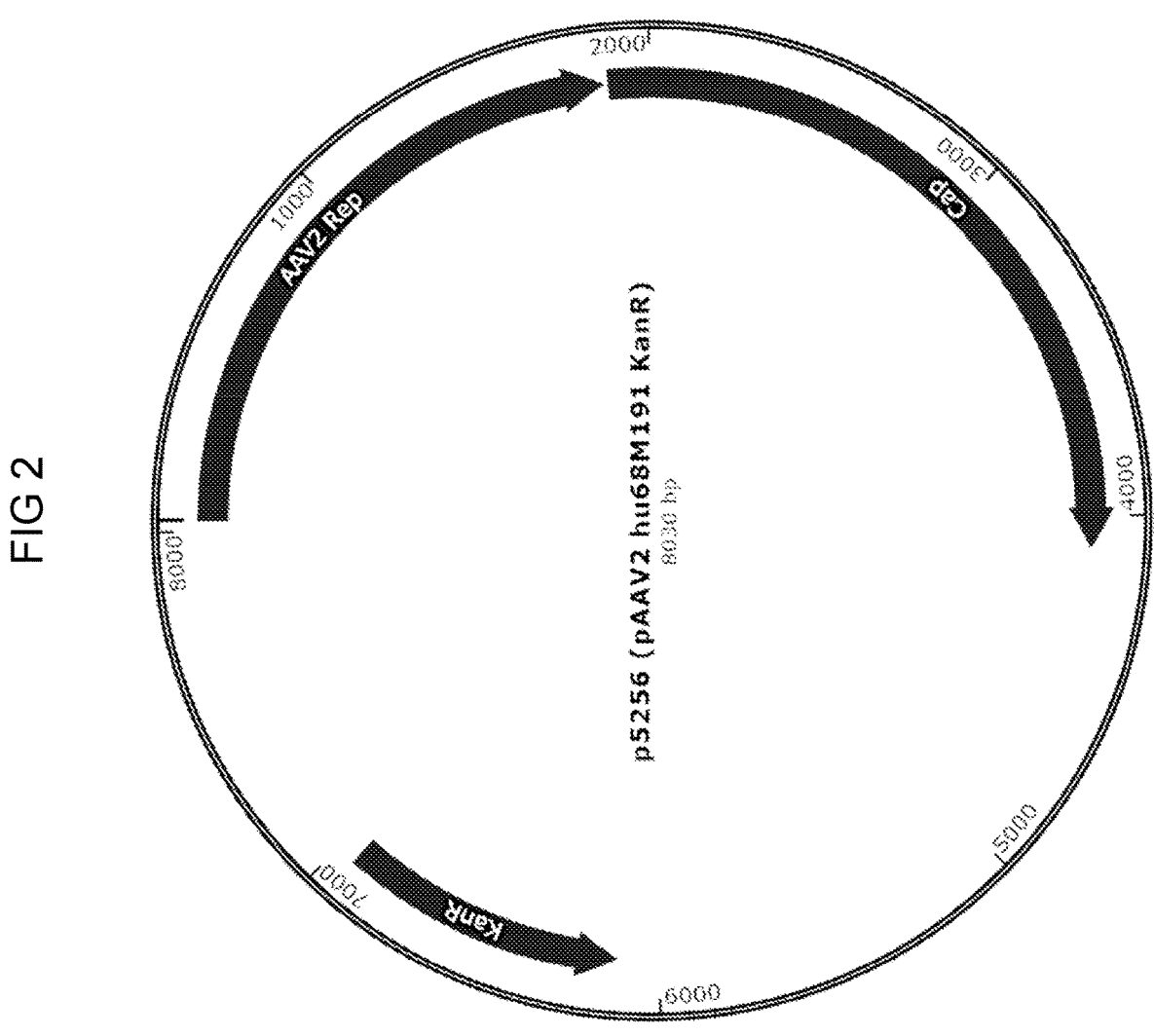
FIG. 2 is a map of a trans plasmid comprising AAV2 rep and AAVhu68M191 cap genes useful for vector production.

Provided herein are novel nucleic acid sequences encoding adeno-associated virus (AAV) hu68 capsid proteins.

These engineered hu68 sequences are referenced interchangeably as AAVhu68M191 and encode the same predicted amino acid sequence as the previously published AAVhu68 coding sequences. These sequences are useful in components and methods for rAAVhu68 production (packaging an AAV vector genome into an AAVhu68 capsid). The use of these novel AAVhu68M191 capsid sequences provides a significant increase in yield of rAAVhu68 vectors compared to production systems using the published AAVhu68 vp1 coding sequence are reproduced in SEQ ID NO: 3. Production systems may utilize these AAVhu68 coding sequences in various cell lines and/or genetic elements for rAAVhu68 vector production, including in production host cells, plasmids (including trans plasmids which may optionally also contain rep sequences) and other genetic elements. The resulting rAAVhu68 vectors may be used for a variety of purposes, including delivery of transgenes and transgene products. Target tissues and organs may include, without limitation, lung, heart, muscle, liver, pancreas, kidney, brain, hippocampus, motor cortex, cerebellum, nasal epithelial cells, cardiac muscle cells or cardiomyocytes, hepatocytes, pulmonary endothelial cells, myocytes, pulmonary epithelial cells, islet cells, acinar cells, renal cells, and motor neurons.

In one embodiment, AAVhu68M191 vp1 has the sequence of SEQ ID NO: 1 or a strand complementary thereto, e.g., the reverse cDNA strand, a complementary mRNA or a complementary tRNA sequence. In certain embodiments, the vp2 and/or vp3 proteins may be expressed additionally or alternatively from different nucleic acid sequences than the vp1, e.g., to alter the ratio of the vp proteins in a selected production system. In certain embodiments, also provided is a nucleic acid sequence which encodes the AAVhu68 vp3 amino acid sequence of SEQ ID NO: 2 (about aa 203 to about aa 736) without the vp1-unique region (about aa 1 to about aa 137) and/or vp2-unique regions (about aa 1 to about aa 202), or a strand complementary thereto, or the corresponding mRNA (about nt 607 to about nt 2211 of SEQ ID NO: 1). In certain embodiments, also provided is a nucleic acid sequence which encodes the AAVhu68 vp2 amino acid sequence of SEQ ID NO: 2 (about aa 138 to about aa 736) without the vp1-unique region (about aa 1 to about 137), or a strand complementary thereto, or the corresponding mRNA (nt 412 to about nt 2211 of SEQ ID NO: 1).

In certain embodiments, AAVhu68M191 has the nucleic acid sequence of SEQ ID NO: 1 or a sequence at least 95% to 99% identical, at least 95%, at least 97%, or at least 99% identical to SEQ ID NO: 1 or a fragment of SEQ ID NO: 1 (e.g., the vp3-encoding region, the vp2-encoding region). In certain embodiments, AAVhu68M191 has the nucleic acid sequence of SEQ ID NO: 1 or a sequence at least 93% to 99%, at least 95%, at least 97%, or at least 99% identical to about nt 412 to about nt 2211 of SEQ ID NO: 1 which encodes the vp2 capsid protein (about aa 138 to 736) of SEQ ID NO: 2. In certain embodiments, AAVhu68M191 has the nucleic acid sequence of about nt 607 to about nt 2211 of SEQ ID NO:1 or a sequence at least 93% to 99%, at least 95%, at least 97%, or at least 99%, identical to SEQ ID NO: 1 which encodes the vp3 capsid protein (about aa 203 to about aa 736) of SEQ ID NO: 2.

A "recombinant AAV" or "rAAV" is a DNAse-resistant viral particle containing two elements, an AAV capsid and a vector genome containing at least non-AAV coding sequences packaged within the AAV capsid. Unless otherwise specified, this term may be used interchangeably with the phrase "rAAV vector". The rAAV is a "replication-defective virus" or "viral vector", as it lacks any functional AAV rep gene or functional AAV cap gene and cannot generate progeny. In certain embodiments, the only AAV sequences are the AAV inverted terminal repeat sequences (ITRs), typically located at the extreme 5' and 3' ends of the vector genome in order to allow the expression cassette containing the gene and regulatory sequences located between the ITRs to be packaged within the AAV capsid.

As used herein, a "vector genome" refers to the nucleic acid sequence packaged inside the rAAV capsid which forms a viral particle. Such a nucleic acid sequence contains AAV inverted terminal repeat sequences (ITRs). In the examples herein, a vector genome contains, at a minimum, from 5' to 3', an AAV 5' ITR, coding sequence(s), and an AAV 3' ITR. ITRs from AAV2, a different source AAV than the capsid, or other than full-length ITRs may be selected. In certain embodiments, the ITRs are from the same AAV source as the AAV which provides the rep function during production or a transcomplementing AAV. Further, other ITRs may be used. Further, the vector genome contains regulatory sequences which direct expression of the gene products. Suitable components of a vector genome are discussed in more detail herein.

A rAAVhu68 vector (i.e., recombinant viral particle) is composed of an AAVhu68 capsid and a vector genome. The AAVhu68 capsid is a T=1 icosahedron composed of 60 total capsid proteins. Typically, expression of the AAVhu68 vp1 capsid gene in a mammalian host cell generates three variable proteins (vp1, corresponding to the full-length protein) and two shorter proteins, vp2 and vp3, which are present at a ratio of ~1:1:10 (vp1:vp2:vp3). In certain production systems, expression of coding sequences encoding vp3-only may be desired in order to obtain the desired ratio of vp1 and vp3 ratio. The resulting AAVhu68 capsid is an assembly of a heterogenous population of vp1, a heterogenous population of vp2, and a heterogenous population of vp3 proteins. As used herein when used to refer to vp capsid proteins, the term "heterogenous" or any grammatical variation thereof, refers to a population consisting of elements that are not the same, for example, having vp1, vp2, or vp3 monomers (proteins) with different modified amino acid sequences. SEQ ID NO: 2 provides the predicted amino acid sequence of the AAVhu68 vp1 protein.

A rAAVhu68 virus stock is population of rAAVhu68 vectors which comprise the AAVhu68 capsid and a vector genome packaged therein.

As used herein, a "subpopulation" of vp proteins refers to a group of vp proteins which has at least one defined characteristic in common and which consists of at least one group member to less than all members of the reference group, unless otherwise specified. For example, a "subpopulation" of vp1 proteins is at least one (1) vp1 protein and less than all vp1 proteins in an assembled AAV capsid, unless otherwise specified. A "subpopulation" of vp3 proteins may be one (1) vp3 protein to less than all vp3 proteins in an assembled AAV capsid, unless otherwise specified. For example, vp1 proteins may be a subpopulation of vp proteins; vp2 proteins may be a separate subpopulation of vp proteins, and vp3 are yet a further subpopulation of vp proteins in an assembled AAV capsid. In another example, vp1, vp2 and vp3 proteins may contain subpopulations having different modifications, e.g., at least one, two, three or four highly deamidated asparagines, e.g., at asparagine— glycine pairs.

As used herein, the term "clade" as it relates to groups of AAV refers to a group of AAV which are phylogenetically related to one another as determined using a Neighbor-Joining algorithm by a bootstrap value of at least 75% (of at least 1000 replicates) and a Poisson correction distance measurement of no more than 0.05, based on alignment of the AAV vp1 amino acid sequence. The Neighbor-Joining algorithm has been described in the literature. See, e.g., M. Nei and S. Kumar, Molecular Evolution and Phylogenetics (Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another clade, or is outside these clades. See, e.g., G Gao, et al, J Virol, 2004 June; 78(10: 6381-6388, which identifies Clades A, B, C, D, E and F, and provides nucleic acid sequences of novel AAV, GenBank Accession Numbers AY530553 to AY530629. See, also, WO 2005/033321.

I. rAAV Vector Production

The novel AAVhu68 capsid coding sequences provided herein are adaptable to a variety of rAAV production systems known in the art. These AAVhu68M191 nucleic acid sequences may be engineered in any suitable nucleic acid molecule for use in rAAV production. These novel AAVhu68 vp1, vp2 and/or vp3 coding sequences may be in a stable or transiently transfected host cell and/or in a genetic element used to produce rAAVhu68. An improved production system comprising host cells for producing a recombinant AAVhu68 comprising the novel AAVhu68M191 coding sequences is further provided herein.

In one embodiment, rAAV are manufactured in culture, suspension, or using an adherent mammalian cell system (e.g., HEK293, Huh-7, or Vero). Any suitable methods for generation of genetic elements used for production of the rAAV may be selected. In certain embodiments, a production host cell contains a nucleic acid which expresses the AAVhu68 capsid protein in the host cell; a nucleic acid molecule suitable for packaging into the AAVhu68 capsid, e.g., a vector genome which contains AAV ITRs and a non-AAV nucleic acid sequence encoding a gene product operably linked to sequences which direct expression of the product in a host cell; and sufficient AAV rep functions and adenovirus helper functions to permit packaging of the nucleic acid molecule into the recombinant AAVhu68 capsid. In one embodiment, the cell culture, suspension, or cell line is composed of mammalian cells (e.g., human embryonic kidney 293 cells (HEK293 cells), among others) or insect cells (e.g., Sf9 cell line or other lines derived from *Spodoptera frugiperda*, or cells derived from other insects, e.g., *Bombyx mori, Mamestra brassicae, Trichoplusia ni,* and *Drosophila melanogaster*). In certain embodiments, the cells are HEK293 cells or derivatives thereof (e.g, HEK293T cells, HEK293F cells), HuH-7 (Huh7) cells, BHK cells, or Vero cells, or derivatives or progeny of any of the above.

A selected genetic element may be delivered to an AAV packaging cell by any suitable method, including transfection, electroporation, liposome delivery, membrane fusion techniques, high velocity DNA-coated pellets, viral infection and protoplast fusion. Additionally or alternatively, stable AAV packaging cells can also be used or made which contain one or more of the required elements for rAAV production described herein, e.g, the novel hu68 cap sequences provided herein. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, NY (2012).

Methods for production of rAAV viral vectors have been described. See, e.g., Gao, et al, Proc. Natl. Acad. Sci. U.S.A. 100 (10), 6081-6086 (2003); US 2013/0045186A1; WO 2003/042397; WO 2005/033321, WO 2006/110689; U.S. Pat. No. 7,588,772 B2. Such a method involves culturing a host cell which contains a nucleic acid sequence encoding an AAV capsid protein; a functional rep gene; an expression cassette composed of, at a minimum, a transgene AAV inverted terminal repeats (ITRs); and sufficient helper functions to permit packaging of the expression cassette into the AAV capsid protein.

In one embodiment, the AAVhu68M191 nucleic acid molecules described herein are useful in a method for packaging a transgene into an AAVhu68 capsid which provides at least a 20% increase in yield of packaged vector as compared to the published AAVhu68 vp1 coding sequence reproduced in SEQ ID NO: 3. In a further embodiment, the AAVhu68M191 nucleic acid molecules described herein are useful in a method for packaging a transgene into an AAVhu68 capsid which provides at least a 30% increase in yield of packaged vector as compared to the published AAVhu68 vp1 coding sequence reproduced in SEQ ID NO: 3. In another embodiment, the AAVhu68M191 nucleic acid molecules described herein are useful in a method of increasing yields of an rAAV and thus, increasing the amount of an rAAV which is present in supernatant prior to, or without requiring cell lysis, is provided.

For use in producing an AAV viral vector (e.g., a recombinant (r) AAV), the expression cassettes can be carried on any suitable vector, e.g., a plasmid, which is delivered to a packaging host cell. The plasmids useful in this invention may be engineered such that they are suitable for replication and packaging in vitro in prokaryotic cells, insect cells, mammalian cells, among others. Suitable transfection techniques and packaging host cells are known and/or can be readily designed by one of skill in the art.

Methods for generating and isolating AAVs suitable for use as vectors are known in the art. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety. For packaging a gene into virions, the ITRs are the only AAV components required in cis in the same construct as the nucleic acid molecule containing the expression cassette(s) to be packaged in the capsid. The cap and rep genes can be supplied in trans. Any of the AAVhu68 or mutant AAV capsid sequences may be under the control of exogenous regulatory control sequences which direct expression thereof in a host cell.

The rep functions are provided from a source AAV which transcomplements the AAV ITRs which flank the extreme 5' and 3' end of the vector genome to permit replication and packaging in the AAV capsid. In certain embodiments, ITRs derived from AAV2 are utilized and AAV2 rep functions are selected. In certain embodiments, at least some of the rep functions are provided by an AAVhu68. See, e.g., the coding sequence for rep52 of AAVhu68 reproduced in SEQ ID NO: 5. The rep52 protein sequence is reproduced in SEQ ID NO: 6. The rep sequences encode the rep proteins of SEQ ID NO: 6, and functional fragments thereof. The AAV rep may be encoded by the nucleic acid sequence of SEQ ID NO: 5. In another embodiment, the rep protein is a heterologous rep protein other than AAVhu68rep, for example but not limited to, AAV1 rep protein, AAV2 rep protein, AAV3 rep protein, AAV4 rep protein, AAV5 rep protein, AAV6 rep protein, AAV7 rep protein, AAV8 rep protein; or rep 78, rep 68, rep 52, rep 40, rep68/78 and rep40/52; or a fragment thereof; or another source. A coding sequence for AAV2 rep functions for replication and packaging into the capsid is provided in SEQ ID NO: 7. The AAV2 rep protein sequence is reproduced in SEQ ID NO: 8.

Typically, rep coding sequences are selected which complement the source of ITRs in the vector genome to be packaged into the capsid to form the viral particle. Thus, if AAV2 5' and 3' ITRs are present in the vector genome (e.g., as carried in a trans plasmid), then AAV2 rep proteins are selected. The rep and cap sequences may be carried by separate genetic elements in the production host cell in culture or suspension. Alternatively, the rep coding sequences may be on the same genetic element as the capsid coding sequences. See, e.g., an illustrative genetic element (e.g., a plasmid) is provided in FIG. 2. The nucleic acid molecule comprising the AAVhu68M191 coding sequences further comprises regulatory sequences (e.g., a promoter) which drives expression of the AAVhu68M191 in the production host cell. Thus, the promoter and regulatory elements are designed and selected for expression in vitro.

An engineered nucleic acid molecule may comprise a spacer sequence between the AAVhu68 vp1 coding sequence and the AAV rep coding sequences. In one embodiment, this sequence is: atgatttaaa tcaggt, SEQ ID NO: 9. Other suitable spacer lengths and sequences may be selected. In certain embodiments, the native AAV p5 promoter, which normally drives rep expression, is located at the 5' end of rep to the 3' end of cap. This arrangement permits a spacer to be inserted between the promoter and the rep gene (i.e., the plasmid backbone), which down-regulate expressions of rep, and increases the ability of the plasmid to support vector production. In certain embodiments, an antibiotic resistance gene is utilized. In certain embodiments, the gene is an ampicillin resistance gene or a kanamycin resistance gene.

In other embodiments, the engineered AAVhu68M191 nucleic acid sequence encoding may be on a genetic element (e.g., a plasmid) which does not contain any rep coding sequences. Such AAVhu68M191 sequences are operably linked to regulatory sequences directing their expression in the production host cell. Any suitable regulatory elements, e.g., a constitutive promoter, a regulatable promoter, an inducible promoter, or the like may be selected for expression in the production cell. For example, without limitation, a constitutive promoter may be selected from a beta actin promoter (chicken or mammalian), SV40, CMV, UBC, EF1A, PGK and CAGG, for mammalian systems, and COPIA and ACT5C for *Drosophila* systems. Still other suitable promoters and regulatory elements are known in the art and may be selected, including elements described herein as suitable for inclusion in the expression cassette for packaging. In certain embodiments, the cap regulatory elements and the expression cassette regulatory elements are different. In other embodiments, one or more of the elements may be the same.

In certain embodiments, the plasmids generated are an AAV cis-plasmid encoding the AAV genome and the gene of interest, an AAV trans-plasmid containing AAV rep and the novel hu68 cap gene, and a helper plasmid. These plasmids may be used in any suitable ratio, e.g., about 1 to about 1 to about 1, based on the total weight of the genetic elements. In other embodiments, the pRepCap to AAV cis-plasmid ratio of about 1:1 by weight of each coding sequence and the pHelper is about 2 times the weight. In other embodiments, the ratio may be about 3 to 1 helper: 10 to 1 pRepCap: 1 to 0.10 rAAV plasmid, by weight. Other suitable ratios may be selected. In certain embodiments, the host cell may be stably transformed with one or more of these elements. For example, the host cell may contain a stable nucleic acid molecule comprising the AAVhu68M191 vp1 coding sequence operably linked to regulatory sequences, a nucleic acid molecule encoding the rep coding sequences and/or one or more nucleic acid molecules encoding helper functions (e.g., adenovirus Ela, or the like). In such embodiments, the various genetic elements may be used in any suitable ratio, e.g., about 1 to about 1 to about 1, based on the total weight of the genetic elements. In certain embodiments, the pRep DNA to Cap DNA to the AAV molecule (e.g., plasmid carrying the vector genome to be packaged) ratio of about 1 to about 1 to about 1 (1:1:1) by weight. In certain embodiments, certain host cells contain some helper elements (e.g., Ad E2a and/or AdE2b) provided in trans and others in cis (e.g., Ad E1a and/or E1b). The helper sequences may be present in about 2 times the amount of the other genetic elements. Still other ratios may be determined.

The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest. In yet another system, the gene therapy vectors are introduced into insect cells by infection with baculovirus-based vectors. For reviews on these production systems, see generally, e.g., Clement and Grieger, Mol Ther Methods Clin Dev, 2016: 3: 16002, published online 2016 Mar. 16. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The crude cell harvest may thereafter be subject method steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector.

A variety of AAV purification methods are known in the art. See, e.g., WO 2017/160360 entitled "Scalable Purification Method for AAV9", which is incorporated by reference herein, and describes methods generally useful for Clade F capsids. A two-step affinity chromatography purification followed by anion exchange resin chromatography are used to purify the vector drug product and to remove empty capsids. The crude cell harvest may be subject steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector. An affinity chromatography purification followed anion exchange resin chromatography are used to purify the vector drug product and to remove empty capsids. In one example, for the Affinity Chromatography step, the diafiltered product may be applied to a Capture Select™ Poros-AAV2/9 affinity resin (Life Technologies) that efficiently captures the AAV2/9 serotype. Under these ionic conditions, a significant percentage of residual cellular DNA and proteins flow through the column, while AAV particles are efficiently captured. See, also, WO2021/158915; WO2019/241535; and WO 2021/165537. Alternatively, other purification methods may be selected.

Methods for characterization or quantification of rAAV are available to one of skill in the art. For example, to calculate empty and full particle content, VP3 band volumes for a selected sample (e.g., in examples herein an iodixanol gradient-purified preparation where # of GC=# of particles) are plotted against GC particles loaded. The resulting linear equation $(y=mx+c)$ is used to calculate the number of particles in the band volumes of the test article peaks. The number of particles (pt) per 20 µL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles.

In certain embodiments, the yield of packaged AAV vector genome copies (VG or GC) may be assessed through use of a bioactivity assay for the encoded transgene. For example, after production, culture supernatants may be collected and spun down to remove cell debris. The yields may be measured by a bioactivity assay using equal volume of the supernatant from a test sample as compared to a control (reference standard) to transduce a selected target cell and to evaluate bioactivity of the encoded protein. Other suitable methods for assessing yield may be selected, including, for example, nanoparticle tracking [Povlich, S. F., et al. (2016) Particle Titer Determination and Characterization of rAAV Molecules Using Nanoparticle Tracking Analysis. Molecular Therapy: AAV Vectors I I, 24(S1), S122], enzyme linked immunosorbent assay (ELISA) [Grimm, D., et al (1999). Titration of AAV-2 particles via a novel capsid ELISA: packaging of genomes can limit production of recombinant AAV-2. Gene therapy, 6(7), 1322-1330. doi.org/10.1038/sj.gt.3300946]; digital droplet (dd) polymerase chain reaction (PCR)Methods for determining single-stranded and self-complementary AAV vector genome titers by digital droplet (dd) polymerase chain reaction (PCR) have been described. See, e.g., M. Lock et al, Hum Gene Ther Methods. 2014 April; 25(2):115-25. doi: 10.1089/hgtb.2013.131. Epub 2014 Feb. 14]. Another suitable method is qPCR. An optimized-PCR method may be used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay. Yet another method is the quantitative DNA dot blot [Wu, Z., et al, (2008). Optimization of self-complementary AAV vectors for liver-directed expression results in sustained correction of hemophilia B at low vector dose. Molecular therapy: the journal of the American Society of Gene Therapy, 16(2), 280-289. doi.org/10.1038/sj.mt.6300355]. Still other methods may be selected.

Methods for assaying for empty capsids and AAV vector particles with packaged genomes have been known in the art. See, e.g., Grimm et al., Gene Therapy (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e., SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used. As used herein, the terms genome copies (GC) and vector genomes (vg) in the context of a dose or dosage (e.g., GC/kg and vg/kg) are meant to be interchangeable.

Methods for determining the ratio among vp1, vp2 and vp3 of capsid protein are also available. See, e.g., Vamseedhar Rayaprolu et al, Comparative Analysis of Adeno-Associated Virus Capsid Stability and Dynamics, J Virol. 2013 December; 87(24): 13150-13160; Buller R M, Rose J A. 1978. Characterization of adenovirus-associated virus-induced polypeptides in KB cells. J. Virol. 25:331-338; and Rose J A, Maizel J V, Inman J K, Shatkin A J. 1971. Structural proteins of adenovirus-associated viruses. J. Virol. 8:766-770.

As used herein, a "stock" of rAAV refers to a population of rAAV. Despite heterogeneity in their capsid proteins due to deamidation, rAAV in a stock are expected to share an identical vector genome. A stock can include rAAV having capsids with, for example, heterogeneous deamidation patterns characteristic of the selected AAV capsid proteins and a selected production system. The stock may be produced from a single production system or pooled from multiple runs of the production system (e.g., different runs of a production system using the same genetic elements for production). A variety of production systems, including but not limited to those described herein, may be selected.

II. rAAV Vectors

As indicated above, the novel AAVhu68 sequences and proteins are useful in production of rAAV. These rAAV are designed to function as antisense delivery vectors, gene therapy vectors, or vaccine vectors.

Genomic sequences which are packaged into an AAV capsid and delivered to a host cell are typically composed of, at a minimum, a transgene and its regulatory sequences, and AAV inverted terminal repeats (ITRs). Both single-stranded AAV and self-complementary (sc) AAV are encompassed with the rAAV. The transgene is a nucleic acid coding sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. In one embodiment, the ITRs are from an AAV different than that supplying a capsid. In one embodiment, the ITR sequences from AAV2. A shortened version of the 5' ITR, termed ΔITR, has been described in which the D-sequence and terminal resolution site (trs) are deleted. In certain embodiments, the vector genome includes a shortened AAV2 ITR of 130 base pairs, wherein the external "a" element is deleted. The shortened ITR is reverted back to the wild-type length of 145 base pairs during vector DNA amplification using the internal A element as a template. In other embodiments, the full-length AAV 5' and 3' ITRs are used. However, ITRs from other AAV sources may be selected. Where the source of the ITRs is from AAV2 and the AAV capsid is from another AAV source, the resulting vector may be termed pseudotyped. However, other configurations of these elements may be suitable.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

The regulatory control elements typically contain a promoter sequence as part of the expression control sequences, e.g., located between the selected 5' ITR sequence and the coding sequence. Constitutive promoters, regulatable promoters [see, e.g., WO 2011/126808 and WO 2013/04943], tissue specific promoters, or a promoter responsive to physiologic cues may be used may be utilized in the vectors described herein. The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rous sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter. In addition to a promoter a vector may contain one or more other appropriate transcription initiation, termination, enhancer sequences, efficient RNA processing signals such as splicing and polyadenylation (polyA) signals; sequences that stabilize cytoplasmic mRNA for example WPRE; sequences that enhance translation efficiency (i.e., Kozak consensus sequence); sequences that enhance protein stability; and when desired, sequences that enhance secretion of the encoded product. An example of a suitable enhancer is the CMV enhancer. Other suitable enhancers include those that are appropriate for desired target tissue indications. In one embodiment, the expression cassette comprises one or more expression enhancers. In one embodiment, the expression cassette contains two or more expression enhancers. These enhancers may be the same or may differ from one another. For example, an enhancer may include a CMV immediate early enhancer. This enhancer may be present in two copies which are located adjacent to one another. Alternatively, the dual copies of the enhancer may be separated by one or more sequences. In still another embodiment, the expression cassette further contains an intron, e.g, the chicken beta-actin intron. Other suitable introns include those known in the art, e.g., such as are described in WO 2011/126808. Examples of suitable polyA sequences include, e.g., SV40, SV50, bovine growth hormone (bGH), human growth hormone, and synthetic polyAs. Optionally, one or more sequences may be selected to stabilize mRNA. An example of such a sequence is a modified WPRE sequence, which may be engineered upstream of the polyA sequence and downstream of the coding sequence [see, e.g., MA Zanta-Boussif, et al, Gene Therapy (2009) 16: 605-619.

Optionally, the vector genome may further comprise drg targeting sequences to modify or extinguish dorsal root ganglia (drg) expression. See, WO 2020/132455; U.S. Provisional Patent Application No. 63/079,290 filed Sep. 16, 2020; U.S. 63/043,562, filed Jun. 24, 2020; U.S. Provisional Patent Applications No. 63/038,488, filed Jun. 12, 2020; and U.S. Provisional Patent Application No. 63/023,593, filed May 12, 2020, which are incorporated herein by reference.

These rAAVs are particularly well suited to gene delivery for therapeutic purposes and for immunization, including inducing protective immunity. Further, the compositions of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

Therapeutic Genes and Gene Products

Useful products encoded by the transgene include a variety of gene products which replace a defective or deficient gene, inactivate or "knock-out", or "knock-down" or reduce the expression of a gene which is expressing at an undesirably high level, or delivering a gene product which has a desired therapeutic effect. In most embodiments, the therapy will be "somatic gene therapy", i.e., transfer of genes to a cell of the body which does not produce sperm or eggs. In certain embodiments, the transgenes express proteins have the sequence of native human sequences. However, in other embodiments, synthetic proteins are expressed. Such proteins may be intended for treatment of humans, or in other embodiments, designed for treatment of animals, including companion animals such as canine or feline populations, or for treatment of livestock or other animals which come into contact with human populations.

Examples of suitable gene products may include those associated with familial hypercholesterolemia, muscular dystrophy, cystic fibrosis, and rare or orphan diseases. Examples of such rare disease may include spinal muscular atrophy (SMA), Huntingdon's Disease, Rett Syndrome (e.g., methyl-CpG-binding protein 2 (MeCP2); UniProtKB—P51608), Amyotrophic Lateral Sclerosis (ALS), Duchenne Type Muscular dystrophy, Friedrichs Ataxia (e.g., frataxin), progranulin (PRGN) (associated with non-Alzheimer's cerebral degenerations, including, frontotemporal dementia (FTD), progressive non-fluent aphasia (PNFA) and semantic dementia), among others. See, e.g., orpha.net/consor/cgi-bin/Disease_Search_List.php; rarediseases.info.nih.gov/diseases.

Examples of suitable genes may include, e.g., hormones and growth and differentiation factors including, without limitation, insulin, glucagon, glucagon-like peptide-1 (GLP1), growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO) (including, e.g., human, canine or feline epo), connective tissue growth factor (CTGF), neutrophic factors including, e.g., basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor α superfamily, including TGFα, activins, inhibins, or any of the bone morphogenic proteins (BMP) BMPs 1-15, any one of the heregluin/neuregulin/

ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-36 (including, e.g., human interleukins IL-1, IL-1α, IL-1β, IL-2, IL-3, IL-4, IL-6, IL-8, IL-12, IL-11, IL-12, IL-13, IL-18, IL-31, IL-35), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. For example, in certain embodiments, the rAAV antibodies may be designed to delivery canine or feline antibodies, e.g., such as anti-IgE, anti-IL31, anti-CD20, anti-NGF, anti-GnRH. Useful gene products also include complement regulatory proteins such as complement regulatory proteins, membrane cofactor protein (MCP), decay accelerating factor (DAF), CR1, CF2, CD59, and C1 esterase inhibitor (C1-INH).

Still other useful gene products include any one of the receptors for the hormones, growth factors, cytokines, lymphokines, regulatory proteins and immune system proteins. The invention encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun,fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase (OTC), arginosuccinate synthetase, arginosuccinate lyase (ASL) for treatment of arginosuccinate lyase deficiency, arginase, fumarylacetate hydrolase, phenylalanine hydroxylase, alpha-1 antitrypsin, rhesus alpha-fetoprotein (AFP), rhesus chorionic gonadotrophin (CG), glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin gene product [e.g., a mini- or micro-dystrophin]. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

In certain embodiments, the rAAV may be used in gene editing systems, which system may involve one rAAV or co-administration of multiple rAAV stocks. For example, the rAAV may be engineered to deliver SpCas9, SaCas9, ARCUS, Cpf1, and other suitable gene editing constructs.

Still other useful gene products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349). In some embodiments, the minigene comprises first 57 base pairs of the Factor VIII heavy chain which encodes the 10 amino acid signal sequence, as well as the human growth hormone (hGH) polyadenylation sequence. In alternative embodiments, the minigene further comprises the A1 and A2 domains, as well as 5 amino acids from the N-terminus of the B domain, and/or 85 amino acids of the C-terminus of the B domain, as well as the A3, C1 and C2 domains. In yet other embodiments, the nucleic acids encoding Factor VIII heavy chain and light chain are provided in a single minigene separated by 42 nucleic acids coding for 14 amino acids of the B domain [U.S. Pat. No. 6,200,560].

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

Further illustrative genes which may be delivered via the rAAV include, without limitation, glucose-6-phosphatase, associated with glycogen storage disease or deficiency type 1A (GSD1), phosphoenolpyruvate-carboxykinase (PEPCK), associated with PEPCK deficiency; cyclin-dependent kinase-like 5 (CDKL5), also known as serine/threonine kinase 9 (STK9) associated with seizures and severe neurodevelopmental impairment; galactose-1 phosphate uridyl transferase, associated with galactosemia; phenylalanine hydroxylase, associated with phenylketonuria (PKU); branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase (OTC), associated with ornithine transcarbamylase deficiency; argininosuccinic acid synthetase (ASS1), associated with citrullinemia; lecithin-cholesterol acyltransferase (LCAT) deficiency: a methylmalonic acidemia (MMA); Niemann-Pick disease, type CI); propionic academia (PA); low density lipoprotein receptor (LDLR) protein, associated with familial hypercholesterolemia (FH); UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyhan syndrome; biotimidase, associated with biotimidase deficiency; alpha-galactosidase A (a-Gal A) associated with Fabry disease); ATP7B associated with Wilson's Disease; beta-glucocerebrosidase, associated with Gaucher disease type 2 and 3; peroxisome membrane protein 70 kDa, associated with Zellweger syndrome; arylsulfatase A (ARSA) associated with metachromatic leukodystrophy, galactocerebrosidase (GALC) enzyme associated with Krabbe disease, alpha-glucosidase (GAA) associated with Pompe disease; sphingomyelinase (SMPD1) gene associated with Nieman Pick disease type A; argininosuccinate synthase associated with adult onset type II citrullinemia (CTLN2); carbamoyl-phosphate synthase 1 (CPS1) associated with urea cycle disorders; survival motor neuron (SMN) protein, associated with spinal muscular atrophy; ceramidase associated with Farber lipogranulomatosis; b-hexosaminidase associated with GM2 gangliosidosis and Tay-Sachs and Sandhoff diseases; aspartylglucosaminidase associated with aspartylglucosaminuria; a-fucosidase associated with fucosidosis; α-mannosidase associated with alpha-mannosidosis; porphobilinogen deaminase, associated with acute intermittent porphyria (AIP); alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, anti-sense to, or a mutant form of, phospholamban, the sarco(endo)plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or mini-dystrophin and utrophin or mini-utrophin for the treatment of muscular dystrophies; and, insulin or GLP-1 for the treatment of diabetes.

Additional genes and diseases of interest include, e.g., dystonin gene related diseases such as Hereditary Sensory and Autonomic Neuropathy Type VI (the DST gene encodes dystonin; dual AAV vectors may be required due to the size of the protein (~7570 aa); SCN9A related diseases, in which loss of function mutants cause inability to feel pain and gain of function mutants cause pain conditions, such as erythromelalgia. Another condition is Charcot-Marie-Tooth type 1F and 2E due to mutations in the NEFL gene (neurofilament light chain). characterized by a progressive peripheral motor and sensory neuropathy with variable clinical and electrophysiologic expression.

In certain embodiments, the rAAV described herein may be used in treatment of mucopolysaccharidoses (MPS) disorders. Such rAAV may contain carry a nucleic acid sequence encoding α-L-iduronidase (IDUA) for treating MPS I (Hurler, Hurler-Scheie and Scheie syndromes); a nucleic acid sequence encoding iduronate-2-sulfatase (IDS) for treating MPS II (Hunter syndrome); a nucleic acid sequence encoding sulfamidase (SGSH) for treating MPSIII A, B, C, and D (Sanfilippo syndrome); a nucleic acid sequence encoding N-acetylgalactosamine-6-sulfate sulfatase (GALNS) for treating MPS IV A and B (Morquio syndrome); a nucleic acid sequence encoding arylsulfatase B (ARSB) for treating MPS VI (Maroteaux-Lamy syndrome); a nucleic acid sequence encoding hyaluronidase for treating MPSI IX (hyaluronidase deficiency) and a nucleic acid sequence encoding beta-glucuronidase for treating MPS VII (Sly syndrome).

In some embodiments, an rAAV vector comprising a nucleic acid encoding a gene product associated with cancer (e.g., tumor suppressors) may be used to treat the cancer, by administering a rAAV harboring the rAAV vector to a subject having the cancer. In some embodiments, an rAAV vector comprising a nucleic acid encoding a small interfering nucleic acid (e.g., shRNAs, miRNAs) that inhibits the expression of a gene product associated with cancer (e.g., oncogenes) may be used to treat the cancer, by administering a rAAV harboring the rAAV vector to a subject having the cancer. In some embodiments, an rAAV vector comprising a nucleic acid encoding a gene product associated with cancer (or a functional RNA that inhibits the expression of a gene associated with cancer) may be used for research purposes, e.g., to study the cancer or to identify therapeutics that treat the cancer. The following is a non-limiting list of exemplary genes known to be associated with the development of cancer (e.g., oncogenes and tumor suppressors): AARS, ABCB1, ABCC4, ABI2, ABL1, ABL2, ACK1, ACP2, ACY1, ADSL, AK1, AKR1C2, AKT1, ALB, ANPEP, ANXA5, ANXA7, AP2M1, APC, ARHGAP5, ARHGEF5, ARID4A, ASNS, ATF4, ATM, ATP5B, ATP5O, AXL, BARD1, BAX, BCL2, BHLHB2, BLMH, BRAF, BRCA1, BRCA2, BTK, CANX, CAP1, CAPN1, CAPNS1, CAV1, CBFB, CBLB, CCL2, CCND1, CCND2, CCND3, CCNE1, CCT5, CCYR61, CD24, CD44, CD59, CDC20, CDC25, CDC25A, CDC25B, CDC2L5, CDK10, CDK4, CDK5, CDK9, CDKL1, CDKN1A, CDKN1B, CDKN1C,

US 12,600,989 B2

19

CDKN2A, CDKN2B, CDKN2D, CEBPG, CENPC1, CGRRF1, CHAF1A, CIB1, CKMT1, CLK1, CLK2, CLK3, CLNS1A, CLTC, COL1A1, COL6A3, COX6C, COX7A2, CRAT, CRHR1, CSF1R, CSK, CSNK1G2, CTNNA1, CTNNB1, CTPS, CTSC, CTSD, CUL1, CYR61, DCC, DCN, DDX10, DEK, DHCR7, DHRS2, DHX8, DLG3, DVL1, DVL3, E2F1, E2F3, E2F5, EGFR, EGR1, EIF5, EPHA2, ERBB2, ERBB3, ERBB4, ERCC3, ETV1, ETV3, ETV6, F2R, FASTK, FBN1, FBN2, FES, FGFR1, FGR, FKBP8, FN1, FOS, FOSL1, FOSL2, FOXG1A, FOXO1A, FRAP1, FRZB, FTL, FZD2, FZD5, FZD9, G22P1, GAS6, GCN5L2, GDF15, GNA13, GNAS, GNB2, GNB2L1, GPR39, GRB2, GSK3A, GSPT1, GTF2I, HDAC1, HDGF, HMMR, HPRT1, HRB, HSPA4, HSPA5, HSPA8, HSPB1, HSPH1, HYAL1, HYOU1, ICAM1, ID1, ID2, IDUA, IER3, IFITMI, IGF1R, IGF2R, IGFBP3, IGFBP4, IGFBP5, IL1B, ILK, ING1, IRF3, ITGA3, ITGA6, ITGB4, JAK1, JARID1A, JUN, JUNB, JUND, K-ALPHA-1, KIT, KITLG, KLK10, KPNA2, KRAS2, KRT18, KRT2A, KRT9, LAMB1, LAMP2, LCK, LCN2, LEP, LITAF, LRPAP1, LTF, LYN, LZTR1, MADH1, MAP2K2, MAP3K8, MAPK12, MAPK13, MAPKAPK3, MAPRE1, MARS, MAS1, MCC, MCM2, MCM4, MDM2, MDM4, MET, MGST1, MICB, MLLT3, MME, MMP1, MMP14, MMP17, MMP2, MNDA, MSH2, MSH6, MT3, MYB, MYBL1, MYBL2, MYC, MYCL1, MYCN, MYD88, MYL9, MYLK, NEO1, NF1, NF2, NFKB1, NFKB2, NFSF7, NID, NINE, NMBR, NME1, NME2, NME3, NOTCH1, NOTCH2, NOTCH4, NPM1, NQO1, NR1D1, NR2F1, NR2F6, NRAS, NRG1, NSEP1, OSM, PA2G4, PABPC1, PCNA, PCTK1, PCTK2, PCTK3, PDGFA, PDGFB, PDGFRA, PDPK1, PEA15, PFDN4, PFDN5, PGAM1, PHB, PIK3CA, PIK3CB, PIK3CG, PIM1, PKM2, PKMYT1, PLK2, PPARD, PPARG, PPIH, PPP1CA, PPP2R5A, PRDX2, PRDX4, PRKAR1A, PRKCBP1, PRNP, PRSS15, PSMA1, PTCH, PTEN, PTGS1, PTMA, PTN, PTPRN, RAB5A, RAC1, RAD50, RAF1, RALBP1, RAP1A, RARA, RARB, RASGRF1, RB1, RBBP4, RBL2, REA, REL, RELA, RELB, RET, RFC2, RGS19, RHOA, RHOB, RHOC, RHOD, RIPK1, RPN2, RPS6 KB1, RRM1, SARS, SELENBP1, SEMA3C, SEMA4D, SEPP1, SERPINHI, SFN, SFPQ, SFRS7, SHB, SHH, SIAH2, SIVA, SIVA TP53, SKI, SKIL, SLC16A1, SLC1A4, SLC20A1, SMO, sphingomyelin phosphodiesterase 1 (SMPD1), SNAI2, SND1, SNRPB2, SOCS1, SOCS3, SOD1, SORT1, SPINT2, SPRY2, SRC, SRPX, STAT1, STAT2, STAT3, STAT5B, STC1, TAF1, TBL3, TBRG4, TCF1, TCF7L2, TFAP2C, TFDP1, TFDP2, TGFA, TGFB1, TGFB1, TGFBR2, TGFBR3, THBS1, TIE, TIMP1, TIMP3, TJP1, TK1, TLE1, TNF, TNFRSF10A, TNFRSF10B, TNFRSF1A, TNFRSF1B, TNFRSF6, TNFSF7, TNK1, TOB1, TP53, TP53BP2, TP5313, TP73, TPBG, TPT1, TRADD, TRAM1, TRRAP, TSG101, TUFM, TXNRD1, TYRO3, UBC, UBE2L6, UCHL1, USP7, VDAC1, VEGF, VHL, VIL2, WEE1, WNT1, WNT2, WNT2B, WNT3, WNT5A, WT1, XRCC1, YES1, YWHAB, YWHAZ, ZAP70, and ZNF9.

A rAAV vector may comprise as a transgene, a nucleic acid encoding a protein or functional RNA that modulates apoptosis. The following is a non-limiting list of genes associated with apoptosis and nucleic acids encoding the products of these genes and their homologues and encoding small interfering nucleic acids (e.g., shRNAs, miRNAs) that inhibit the expression of these genes and their homologues are useful as transgenes in certain embodiments of the invention: RPS27A, ABL1, AKT1, APAF1, BAD, BAGI, BAG3, BAG4, BAK1, BAX, BCL10, BCL2, BCL2A1, BCL2L1, BCL2L10, BCL2L11, BCL2L12, BCL2L13,

20

BCL2L2, BCLAF1, BFAR, BID, BIK, NAIP, BIRC2, BIRC3, XIAP, BIRC5, BIRC6, BIRC7, BIRC8, BNIP1, BNIP2, BNIP3, BNIP3L, BOK, BRAF, CARD10, CARD11, NLRC4, CARD14, NOD2, NOD1, CARD6, CARDS, CARDS, CASP1, CASP10, CASP14, CASP2, CASP3, CASP4, CASP5, CASP6, CASP7, CASP8, CASP9, CFLAR, CIDEA, CIDEB, CRADD, DAPK1, DAPK2, DFFA, DFFB, FADD, GADD45A, GDNF, HRK, IGF1R, LTA, LTBR, MCL1, NOL3, PYCARD, RIPK1, RIPK2, TNF, TNFRSF10A, TNFRSF10B, TNFRSF10C, TNFRSF10D, TNFRSF11B, TNFRSF12A, TNFRSF14, TNFRSF19, TNFRSF1A, TNFRSF1B, TNFRSF21, TNFRSF25, CD40, FAS, TNFRSF6B, CD27, TNFRSF9, TNFSF10, TNFSF14, TNFSF18, CD40LG, FASLG, CD70, TNFSF8, TNFSF9, TP53, TP53BP2, TP73, TP63, TRADD, TRAF1, TRAF2, TRAF3, TRAF4, and TRAF5.

Useful gene products also include miRNAs, miRNA sponges, antisense oligonucleotides, and TuD RNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The rAAV may include genes encoding antibodies, and particularly neutralizing antibodies against a viral pathogen or soluble decoy proteins mimicking the viral ligand. Such anti-viral antibodies may include anti-SARS antibodies, including anti-SARS-CoV2 (Covid-19) or anti-SARS-CoV2, anti-influenza antibodies directed against one or more of Influenza A, Influenza B, and Influenza C. Other anti-SARS constructs such as the soluble Ace2 decoy proteins described in, e.g., U.S. Patent Application No. 63/002, 100, filed Mar. 30, 2020; U.S. Patent Application No. 63/027,731, filed May 20, 2020; U.S. Provisional Patent Application No. 63/069,651, filed Aug. 24, 2020.

Anti-viral antibodies may be targeted to other virulent human pathogens. The serotypes of influenza A which have been associated with pandemics include, HIN1, which caused Spanish Flu in 1918, and Swine Flu in 2009; H2N2, which caused Asian Flu in 1957; H3N2, which caused Hong Kong Flu in 1968; H5N1, which caused Bird Flu in 2004; H7N7; H1N2; H9N2; H7N2; H7N3; and H10N7. Other target pathogenic viruses include, arenaviruses (including funin, machupo, and Lassa), filoviruses (including Marburg and Ebola), hantaviruses, picornoviridae (including rhinoviruses, echovirus), coronaviruses, paramyxovirus, morbillivirus, respiratory syncytial virus, togavirus, coxsackievirus, JC virus, parvovirus B19, parainfluenza, adenoviruses, reoviruses, variola (Variola major (Smallpox)) and Vaccinia (Cowpox) from the poxvirus family, and varicella-zoster (pseudorabies). Viral hemorrhagic fevers are caused by members of the arenavirus family (Lassa fever) (which family is also associated with Lymphocytic choriomeningitis (LCM)), filovirus (ebola virus), and hantavirus (puremala). The members of picornavirus (a subfamily of rhinoviruses), are associated with the common cold in humans. The coronavirus family, which includes a number of non-human viruses such as infectious bronchitis virus (poultry), porcine transmissible gastroenteric virus (pig), porcine hemagglutinatin encephalomyelitis virus (pig), feline infectious peritonitis virus (cat), feline enteric coronavirus (cat), canine coronavirus (dog). The human respiratory coronaviruses, have been putatively associated with the common cold, non-A, B or C hepatitis, and sudden acute respiratory syndrome (SARS). The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus (RSV). The parvovirus family includes feline parvovirus (feline enteritis), feline panleucopenia virus, canine parvovirus, and porcine parvovirus. The adenovirus family includes viruses (EX, AD7, ARD, O.B.) which cause respiratory disease. Thus, in certain embodiments, a rAAV vector as described herein may be engineered to express an anti-ebola antibody, e.g., 2G4, 4G7, 13C6, an anti-influenza antibody, e.g., F16, CR8033, and anti-RSV antibody, e.g, palivizumab, motavizumab.

A neutralizing antibody construct against a bacterial pathogen may also be selected for use in the present invention. In one embodiment, the neutralizing antibody construct is directed against the bacteria itself. In another embodiment, the neutralizing antibody construct is directed against a toxin produced by the bacteria. Examples of airborne bacterial pathogens include, e.g., *Neisseria meningitidis* (meningitis), *Klebsiella pneumonia* (pneumonia), *Pseudomonas aeruginosa* (pneumonia), *Pseudomonas pseudomallei* (pneumonia), *Pseudomonas mallei* (pneumonia), *Acinetobacter* (pneumonia), *Moraxella catarrhalis, Moraxella lacunata, Alkaligenes, Cardiobacterium, Haemophilus influenzae* (flu), *Haemophilus parainfluenzae, Bordetella pertussis* (whooping cough), *Francisella tularensis* (pneumonia/fever), *Legionella* pneumonia (Legionnaires disease), *Chlamydia psittaci* (pneumonia), *Chlamydia pneumoniae* (pneumonia), *Mycobacterium tuberculosis* (tuberculosis (TB)), *Mycobacterium kansasii* (TB), *Mycobacterium avium* (pneumonia), *Nocardia asteroides* (pneumonia), *Bacillus anthracis* (anthrax), *Staphylococcus aureus* (pneumonia), *Streptococcus pyogenes* (scarlet fever), *Streptococcus pneumoniae* (pneumonia), *Corynebacteria diphtheria* (diphtheria), *Mycoplasma pneumoniae* (pneumonia).

The rAAV may include genes encoding antibodies, and particularly neutralizing antibodies against a bacterial pathogen such as the causative agent of anthrax, a toxin produced by *Bacillus anthracis*. Neutralizing antibodies against protective agent (PA), one of the three peptides which form the toxoid, have been described. The other two polypeptides consist of lethal factor (LF) and edema factor (EF). Anti-PA neutralizing antibodies have been described as being effective in passively immunization against anthrax. See, e.g., U.S. Pat. No. 7,442,373; R. Sawada-Hirai et al, J Immune Based Ther Vaccines. 2004; 2: 5. (on-line 2004 May 12). Still other anti-anthrax toxin neutralizing antibodies have been described and/or may be generated. Similarly, neutralizing antibodies against other bacteria and/or bacterial toxins may be used to generate an AAV-delivered anti-pathogen construct as described herein.

Antibodies against infectious diseases may be caused by parasites or by fungi, including, e.g., *Aspergillus* species, *Absidia corymbifera, Rhixpus stolonifer, Mucor plumbeaus, Cryptococcus neoformans, Histoplasm capsulatum, Blastomyces dermatitidis, Coccidioides immitis, Penicillium* species, *Micropolyspora faeni, Thermoactinomyces vulgaris,* *Alternaria alternate, Cladosporium species, Helminthosporium,* and *Stachybotrys* species.

The rAAV may include genes encoding antibodies, and particularly neutralizing antibodies, against pathogenic factors of diseases such as Alzheimer's disease (AD), Parkinson's disease (PD), GBA-Parkinson's, Rheumatoid arthritis (RA), Irritable bowel syndrome (IBS), chronic obstructive pulmonary disease (COPD), cancers, tumors, systemic sclerosis, asthma and other diseases. Such antibodies may be., without limitation, e.g., alpha-synuclein, anti-vascular endothelial growth factor (VEGF) (anti-VEGF), anti-VEGFA, anti-PD-1, anti-PDL1, anti-CTLA-4, anti-TNF-alpha, anti-IL-17, anti-IL-23, anti-IL-21, anti-IL-6, anti-IL-6 receptor, anti-IL-5, anti-IL-7, anti-Factor XII, anti-IL-2, anti-HIV, anti-IgE, anti-tumour necrosis factor receptor-1 (TNFR1), anti-notch 2/3, anti-notch 1, anti-OX40, anti-erb-b2 receptor tyrosine kinase 3 (ErbB3), anti-ErbB2, anti-beta cell maturation antigen, anti-B lymphocyte stimulator, anti-CD20, anti-HER2, anti-granulocyte macrophage colony-stimulating factor, anti-oncostatin M (OSM), anti-lymphocyte activation gene 3 (LAG3) protein, anti-CCL20, anti-serum amyloid P component (SAP), anti-prolyl hydroxylase inhibitor, anti-CD38, anti-glycoprotein IIb/IIIa, anti-CD52, anti-CD30, anti-IL-1beta, anti-epidermal growth factor receptor, anti-CD25, anti-RANK ligand, anti-complement system protein C5, anti-CD11a, anti-CD3 receptor, anti-alpha-4 (a4) integrin, anti-RSV F protein, and anti-integrin $\alpha_4\beta_7$. Still other pathogens and diseases will be apparent to one of skill in the art. Other suitable antibodies may include those useful for treating Alzheimer's Disease, such as, e.g., anti-beta-amyloid (e.g., crenezumab, solanezumab, aducanumab), anti-beta-amyloid fibril, anti-beta-amyloid plaques, anti-tau, a bapineuzamab, among others. Other suitable antibodies for treating a variety of indications include those described, e.g., in PCT/US2016/058968, filed 27 Oct. 2016, published as WO 2017/075119A1.

III. Compositions and Uses

Provided herein are compositions containing at least one rAAV stock (e.g., an rAAVhu68 stock or a mutant rAAV stock) generated using the novel AAVhu68M191 cap sequences provided herein and an optional carrier, excipient and/or preservative.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host. Delivery vehicles such as liposomes, nanocapsules, microparticles, microspheres, lipid particles, vesicles, and the like, may be used for the introduction of the compositions of the present invention into suitable host cells. In particular, the rAAV vector delivered vector genomes may be formulated for delivery either encapsulated in a lipid particle, a liposome, a vesicle, a nanosphere, or a nanoparticle or the like.

In one embodiment, a composition includes a final formulation suitable for delivery to a subject, e.g., is an aqueous liquid suspension buffered to a physiologically compatible pH and salt concentration. Optionally, one or more surfactants are present in the formulation. In another embodiment, the composition may be transported as a concentrate which is diluted for administration to a subject. In other embodiments, the composition may be lyophilized and reconstituted at the time of administration.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery), lung, heart, eye, kidney), oral, inhalation, intranasal, intrathecal, intratracheal, intraarterial, intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 25 to about 1000 microliters to about 100 mL of solution containing concentrations of from about $1 \times 10^9$ to $1 \times 10^{16}$ genomes virus vector. The dosage will be adjusted to balance the therapeutic benefit against any side effects and such dosages may vary depending upon the therapeutic application for which the recombinant vector is employed. The levels of expression of the transgene product can be monitored to determine the frequency of dosage resulting in viral vectors, preferably AAV vectors containing the minigene. Optionally, dosage regimens similar to those described for therapeutic purposes may be utilized for immunization using the compositions of the invention.

The replication-defective virus compositions can be formulated in dosage units to contain an amount of replication-defective virus that is in the range of about $1.0 \times 10^9$ GC to about $1.0 \times 10^{16}$ GC (to treat an average subject of 70 kg in body weight) including all integers or fractional amounts within the range, and preferably $1.0 \times 10^{12}$ GC to $1.0 \times 10^{14}$ GC for a human patient. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{10}$, $3 \times 10^{11}$, $4 \times 10^{11}$, $5 \times 10^{11}$, $6 \times 10^{11}$, $7 \times 10^{11}$, $8 \times 10^1$, or $9 \times 10^1$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range.

These above doses may be administered in a variety of volumes of carrier, excipient or buffer formulation, ranging from about 25 to about 1000 microliters, or higher volumes, including all numbers within the range, depending on the size of the area to be treated, the viral titer used, the route of administration, and the desired effect of the method. In one embodiment, the volume of carrier, excipient or buffer is at least about 25 μL. In one embodiment, the volume is about 50 μL. In another embodiment, the volume is about 75 μL. In another embodiment, the volume is about 100 μL. In another embodiment, the volume is about 125 μL. In another embodiment, the volume is about 150 μL. In another embodiment, the volume is about 175 μL. In yet another embodiment, the volume is about 200 μL. In another embodiment, the volume is about 225 μL. In yet another embodiment, the volume is about 250 μL. In yet another embodiment, the volume is about 275 μL. In yet another embodiment, the volume is about 300 μL. In yet another embodiment, the volume is about 325 μL. In another embodiment, the volume is about 350 μL. In another embodiment, the volume is about 375 μL. In another embodiment, the volume is about 400 μL. In another embodiment, the volume is about 450 μL. In another embodiment, the volume is about 500 μL. In another embodiment, the volume is about 550 μL. In another embodiment, the volume is about 600 μL. In another embodiment, the volume is about 650 μL. In another embodiment, the volume is about 700 μL. In another embodiment, the volume is between about 700 and 1000 μL.

In certain embodiments, the dose may be in the range of about $1 \times 10^9$ GC/g brain mass to about $1 \times 10^{12}$ GC/g brain mass. In certain embodiments, the dose may be in the range of about $3 \times 10^{10}$ GC/g brain mass to about $3 \times 10^{11}$ GC/g brain mass. In certain embodiments, the dose may be in the range of about $5 \times 10^{10}$ GC/g brain mass to about $1.85 \times 10^{11}$ GC/g brain mass.

In one embodiment, the viral constructs may be delivered in doses of from at least about least $1 \times 10^9$ GCs to about $1 \times 10^{15}$, or about $1 \times 10^{11}$ to $5 \times 10^{13}$ GC. Suitable volumes for delivery of these doses and concentrations may be determined by one of skill in the art. For example, volumes of about 1 μL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage will be adjusted to balance the therapeutic benefit against any side effects and such dosages may vary depending upon the therapeutic application for which the recombinant vector is employed.

The above-described recombinant vectors may be delivered to host cells according to published methods. The rAAV, preferably suspended in a physiologically compatible carrier, may be administered to a human or non-human mammalian patient. In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous delivery, a pH of about 6.8 to about 7.2 may be desired. However, other pHs within the broadest ranges and these subranges may be selected for other route of delivery.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo. A suitable surfactant, or combination of surfactants, may be selected from among non-ionic surfactants that are nontoxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy-oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension. In one example, the formulation may contain, e.g., buffered saline solution comprising one or more of sodium chloride, sodium bicarbonate, dextrose, magnesium sulfate (e.g., magnesium sulfate·$7H_2O$), potassium chloride, calcium chloride (e.g., calcium chloride·$2H_2O$), dibasic sodium phosphate, and mixtures thereof, in water. Suitably, for intrathecal delivery, the osmolarity is within a range compatible with cerebrospinal fluid (e.g., about 275 to about 290); see, e.g., emedicine.medscape.com/article/2093316-overview. Optionally, for intrathecal delivery, a commercially available diluent may be used as a suspending agent, or in combination with another suspending agent and other optional excipients. See, e.g., Elliotts B® solution [Lukare Medical]. In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, Ommaya reservoir or for delivery by another device or route. In one example, the composition is formulated for intrathecal delivery.

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipital/intracisternal, and/or C1-2 puncture. For example, material may be introduced for diffusion throughout the subarachnoid space by means of lumbar puncture. In another example, injection may be into the cisterna magna.

As used herein, the terms "intracisternal delivery" or "intracisternal administration" refer to a route of administration for drugs directly into the cerebrospinal fluid of the cisterna magna cerebellomedularis, more specifically via a suboccipital puncture or by direct injection into the cisterna magna or via permanently positioned tube.

As used herein, "encoded amino acid sequence" refers to the amino acid which is predicted based on the translation of a known DNA codon of a referenced nucleic acid sequence being translated to an amino acid. The following table illustrates DNA codons and twenty common amino acids, showing both the single letter code (SLC) and three letter code (3LC).

| Amino Acid | SLC | 3 LC | DNA codons |
|---|---|---|---|
| Isoleucine | I | Ile | ATT, ATC, ATA |
| Leucine | L | Leu | CTT, CTC, CTA, CTG, TTA, TTG |
| Valine | V | Val | GTT, GTC, GTA, GTG |

-continued

| Amino Acid | SLC | 3 LC | DNA codons |
|---|---|---|---|
| Phenylalanine | F | Phe | TTT, TTC |
| Methionine | M | Met | ATG |
| Cysteine | C | Cys | TGT, TGC |
| Alanine | A | Ala | GCT, GCC, GCA, GCG |
| Glycine | G | Gly | GGT, GGC, GGA, GGG |
| Proline | P | Pro | CCT, CCC, CCA, CCG |
| Threonine | T | Thr | ACT, ACC, ACA, ACG |
| Serine | S | Ser | TCT, TCC, TCA, TCG, AGT, AGC |
| Tyrosine | Y | Tyr | TAT, TAC |
| Tryptophan | W | Trp | TGG |
| Glutamine | Q | Gln | CAA, CAG |
| Asparagine | N | Asn | AAT, AAC |
| Histidine | H | His | CAT, CAC |
| Glutamic acid | E | Glu | GAA, GAG |
| Aspartic acid | D | Asp | GAT, GAC |
| Lysine | K | Lys | AAA, AAG |
| Arginine | R | Arg | CGT, CGC, CGA, CGG, AGA, AGG |
| Stop codons | Stop | | TAA, TAG, TGA |

As used herein, an "AAVhu68 capsid" is a self-assembled AAV capsid composed of multiple AAVhu68 vp proteins. In certain embodiments, "AAVhu68 capsid" includes an AAV having a capsid protein produced using a nucleic acid sequence encoding the predicted amino acid sequence of SEQ ID NO: 2.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g., of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length and may be up to about 700 amino acids. Examples of suitable fragments are described herein.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. In the examples, AAV alignments are performed using the published AAV9 sequences as a reference point. Alignments are performed using any of a variety of publicly or commercially available Multiple Sequence Alignment Programs. Examples of such programs include, "Clustal Omega", "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6. 1, herein incorporated by reference. Multiple sequence alignment programs are also available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13): 2682-2690 (1999).

The term "AAV intermediate" or "AAV vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product.

A "genetic element" includes any nucleic acid molecule, e.g., naked DNA, a plasmid, phage, transposon, cosmid, episome, virus, etc., which transfers the sequences carried thereon. Optionally, such a genetic element may utilize a lipid-based carrier. Unless otherwise specified, the genetic element may be delivered by any suitable method, including transfection, electroporation, liposome delivery, membrane fusion techniques, high velocity DNA-coated pellets, viral infection and protoplast fusion.

A "stable host cell" for rAAV production is a host cell with had been engineered to contain one or more of the required rAAV production elements (e.g., minigene, rep sequences, the AAVhu68 engineered cap sequences as defined herein, and/or helper functions) and its progeny. A stable host cell may contain the required component(s)

under the control of an inducible promoter. Alternatively, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from HEK293 cells (which contain E1 helper functions under the control of a constitutive promoter), Huh7 cells, Vero cells, engineered to contain helper functions under the control of a suitable promoter, which optionally further contains the rep and/or cap proteins under the control of inducible promoters. Still other stable host cells may be generated by one of skill in the art.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% (±10%, e.g., ±1, ±2, ±3, ±4, ±5, ±6, ±7, ±8, ±9, ±10, or values therebetween) from the reference given, unless otherwise specified.

As used herein, "disease", "disorder" and "condition" are used interchangeably, to indicate an abnormal state in a subject.

The term "expression" is used herein in its broadest meaning and comprises the production of RNA or of RNA and protein. With respect to RNA, the term "expression" or "translation" relates in particular to the production of peptides or proteins. Expression may be transient or may be stable.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

As used herein, an "expression cassette" refers to a nucleic acid molecule which comprises a biologically useful nucleic acid sequence (e.g., a gene cDNA encoding a protein, enzyme or other useful gene product, mRNA, etc.) and regulatory sequences operably linked thereto which direct or modulate transcription, translation, and/or expression of the nucleic acid sequence and its gene product. As used herein, "operably linked" sequences include both regulatory sequences that are contiguous or non-contiguous with the nucleic acid sequence and regulatory sequences that act in trans or cis nucleic acid sequence. Such regulatory sequences typically include, e.g., one or more of a promoter, an enhancer, an intron, a Kozak sequence, a polyadenylation sequence, and a TATA signal. The expression cassette may contain regulatory sequences upstream (5' to) of the gene sequence, e.g., one or more of a promoter, an enhancer, an intron, etc., and one or more of an enhancer, or regulatory sequences downstream (3' to) a gene sequence, e.g., 3' untranslated region (3' UTR) comprising a polyadenylation site, among other elements. In certain embodiments, the regulatory sequences are operably linked to the nucleic acid sequence of a gene product, wherein the regulatory sequences are separated from nucleic acid sequence of a gene product by an intervening nucleic acid sequences, i.e., 5'-untranslated regions (5'UTR). In certain embodiments, the expression cassette comprises nucleic acid sequence of one or more of gene products. In some embodiments, the expression cassette can be a monocistronic or a bicistronic expression cassette. In other embodiments, the term "transgene" refers to one or more DNA sequences from an exogenous source which are inserted into a target or a host cell. In certain embodiments, a vector genome may contain two or more expression cassettes. Typically, such an expression cassette for generating a viral vector contains the coding sequence for the gene product described herein flanked by packaging signals of the viral genome and other expression control sequences such as those described herein.

The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

As used herein, the term "operably linked" refers to both expression control sequences that are contiguous with the gene of interest and expression control sequences that act in trans or at a distance to control the gene of interest.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the gene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In many instances, rAAV particles are referred to as DNase resistant. However, in addition to this endonuclease (DNase), other endo- and exo-nucleases may also be used in the purification steps described herein, to remove contaminating nucleic acids. Such nucleases may be selected to degrade single stranded DNA and/or double-stranded DNA, and RNA. Such steps may contain a single nuclease, or mixtures of nucleases directed to different targets, and may be endonucleases or exonucleases.

The term "nuclease-resistant" indicates that the AAV capsid has fully assembled around the expression cassette which is designed to deliver a gene to a host cell and protects these packaged genomic sequences from degradation (digestion) during nuclease incubation steps designed to remove contaminating nucleic acids which may be present from the production process.

As used herein, an "effective amount" refers to the amount of the rAAV composition which delivers and expresses in the target cells an amount of the gene product from the vector genome. An effective amount may be determined based on an animal model, rather than a human patient. Examples of a suitable murine model are described herein.

The term "translation" in the context of the present invention relates to a process at the ribosome, wherein an mRNA strand controls the assembly of an amino acid sequence to generate a protein or a peptide.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

EXAMPLES

Example 1

The native sequence of the AAVhu68 capsid gene was engineered. This new coding sequence [SEQ ID NO: 1; also termed herein AAVhu68M191, hu68M191, or M191] encodes the same protein sequence as the previously published AAVhu68 capsid gene (reproduced in SEQ ID NO: 3), but having 191 bp differences from the native sequence of AAVhu68. The AAVhu68M191 sequence of SEQ ID NO: 1 was engineered into a plasmid backbone containing 4 wild type AAV2 rep genes, where the AAVhu68M191 vp1 coding sequence for the AAV capsid proteins replaced the native AAVhu68 cap gene. The map shown in FIG. 2 depicts the plasmid named pAAV2/hu68M191 used for generating rAAV. The plasmid contains a Col E1 ori, a kanamycin resistance gene, the AAV2 rep coding sequences, and the AAVhu68M191 coding sequence. The AAV p5 promoter, which normally drives rep expression, is moved in this construct from the 5' end of rep to the 3' end of cap. For triple transfection, a plasmid containing adenoviral helper functions is used. Plasmid pAdDeltaF6(KanR) contains the regions of adenovirus genome that are important for AAV replication; namely, E2A, E4, and VA RNA (the adenovirus E1 functions are provided by the HEK293 cells). However, the plasmid does not contain other adenovirus replication or structural genes. The plasmid does not contain the cis elements critical for replication, such as the adenoviral ITRs;

therefore, no infectious adenovirus is expected to be generated. The plasmid was derived from an E1, E3-deleted molecular clone of Ad5 (pBHG10, a pBR322-based plasmid). Deletions were introduced into Ad5 to eliminate expression of unnecessary adenovirus genes and reduce the amount of adenovirus DNA from 32 kb to 12 kb. Finally, a kanamycin resistance gene is provided. The E2, E4, and VA adenoviral genes that remain in this plasmid, along with E1, which is present in HEK293 cells, are necessary for AAV vector production.

For CellSTACK® scale production, rAAV vectors were produced and purified with the protocol described by Lock et al [Lock, Martin, et al. "Rapid, Simple, and Versatile Manufacturing of Recombinant Adeno-Associated Viral Vectors at Scale." Human Gene Therapy 21:1259-1271 (October 2010).] The titers of the purified products were measured by Droplet Digital PCR described by Lock et al [Lock, Martin, et al. "Absolute Determination of Single-Stranded and Self-Complementary Adeno-Associated Viral Vector Genome Titers by Droplet Digital PCR." Human Gene Therapy 25:115-125 (April 2014).] The three plasmids used in the triple-transfection part of the protocol were: adenovirus helper plasmid pAdΔF6, a trans plasmid carrying AAV2 rep gene and the capsid gene of the desired AAV type, and a cis plasmid carrying a transgene cassette flanked by AAV2 5' and 3' ITRs. The trans plasmids used here were either pAAV2/hu68 or pAAV2/hu68M191. The cis plasmid used here was pAAV.CB7.CI.eGFP.WPRE.rBG.

For 12-well plate scale production, the protocol was adapted from the CellSTACK® protocol mentioned above, without the purification step, mainly by reducing the materials used proportionally to cell culture areas. The trans plasmids used here were pAAV2/hu68, pAAV2/hu68M191 or pAAV2/9. The cis plasmid used here was pAAV.CB7.CI. ffLuciferase.rBG. After production, culture supernatants were collected and spun down to remove cell debris. The yields were then measured by a bioactivity assay: equal volume of the supernatants was used to transduce Huh-7 cells and luciferase activity was measured with a luminometer (BioTek).

CellSTACK® production data is shown in the following table. All the three preps were small scale production. "E+ #" refers to the exponent which follows the E+ in numerical value, e.g., E+13 refers to "×10^{13}" "CS" means CellSTACK®. "GC" means vector genome copies.

| Vector Name | Yield per CS (GC) |
|---|---|
| AAVhu68M191.CB7.CI.eGFP.WPRE.rBG | 6.63E+13 |
| AAVhu68M191.CB7.CI.eGFP.WPRE.rBG | 4.71E+13 |
| AAVhu68M191.CB7.CI.eGFP.WPRE.rBG | 6.33E+13 |

Comparative data with the same cis plasmid having the previously published AAVhu68 sequence is provided in the following table. "E+ #" refers to the exponent which follows the E+ in numerical value, e.g., E+14 is "×10^{14}".

| Vector Name | Production scale | # of CS used | Yield per CS (GC) |
|---|---|---|---|
| AAVhu68.CB7.CI.eGFP.WPRE.rBG(p1963) | small (1 CS) | 1 | 3.69E+13 |
| AAVhu68.CB7.CI.eGFP.WPRE.rBG(p1963) | small (1 CS) | 1 | 3.22E+13 |

-continued

| Vector Name | Production scale | # of CS used | Yield per CS (GC) |
|---|---|---|---|
| AAVhu68.CB7.CI.eGFP.WPRE.rBG(p1963) | small (1 CS) | 1 | 2.98E+13 |
| AAVhu68.CB7.CI.eGFP.WPRE.rBG(p1963) | Midi (2 CS) | 2 | 5.80E+13 |
| AAVhu68.CB7.CI.eGFP.WPRE.rBG(p1963) | Midi (2 CS) | 2 | 3.06E+13 |
| AAVhu68.CB7.CI.eGFP.WPRE.rBG(p1963) | Midi (2 CS) | 2 | 3.08E+13 |
| AAVhu68.CB7.CI.eGFP.WPRE.rBG(p1963) | Mega (6 CS) | 6 | 5.73E+13 |
| AAVhu68.CB7.CI.eGFP.WPRE.rBG(p1963) | Mega (6 CS) | 6 | 5.72E+13 |

Figure 3A:
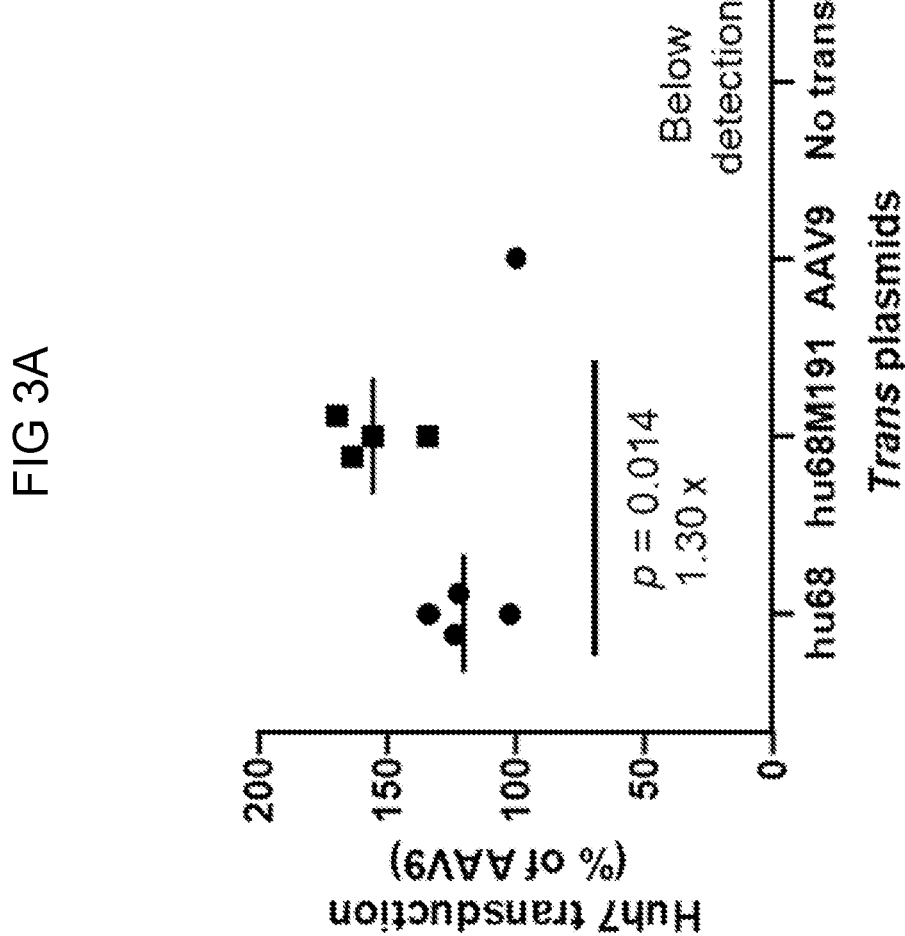
FIGS. 3A and 3B illustrate production yields of rAAV having a marker gene produced using the pAAV2/AAVhu68 cap plasmid containing the engineered AAVhu68M191 (hu68M191) nucleic acid sequence of SEQ ID NO: 1.
Figure 3B:
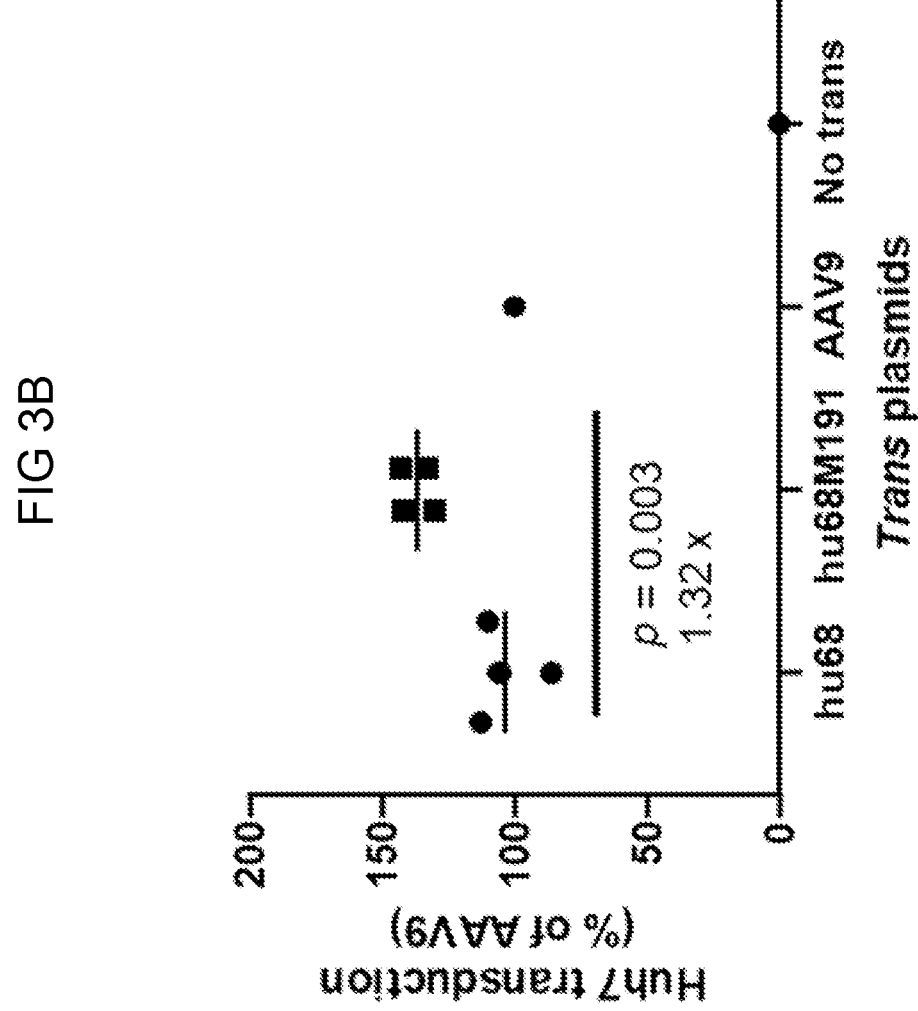
Figure 4:
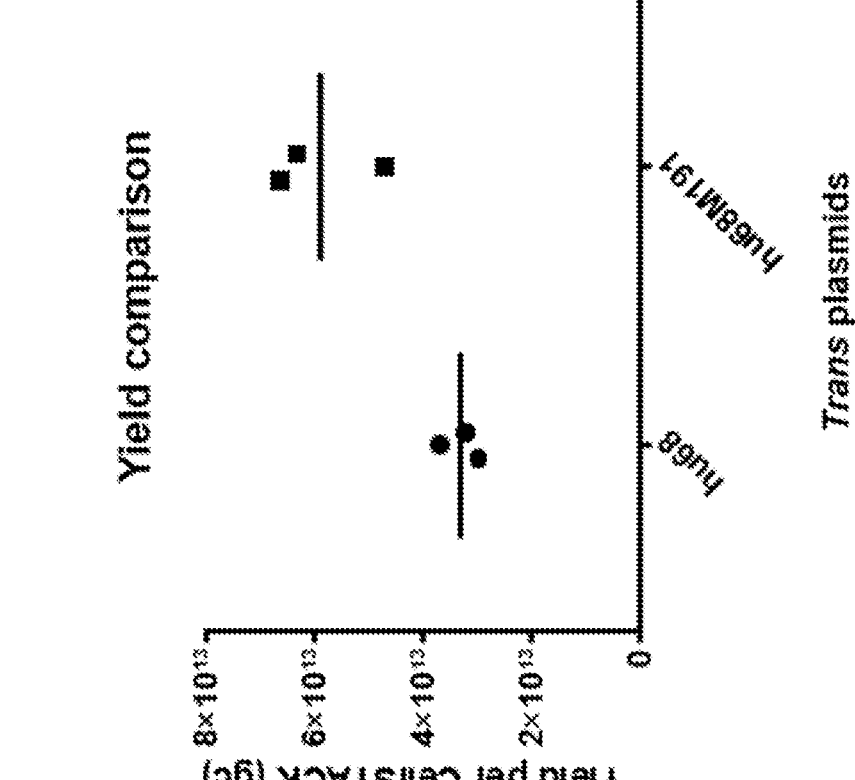
FIG. 4 shows higher yield for an rAAV viral particle produced using a plasmid containing the AAVhu68M191 (hu68M191) coding sequence in the triple transfection production system, as compared to a rAAV viral particle produced using a plasmid encoding the AAV2 rep proteins and the native AAVhu68 (hu68) coding sequence. This data is from a CellSTACK® scale production system. The cis plasmid packaged contained the same transgene cassette, CB7.CI.eGFP.WPRE.RBG, for both vectors. Triple transfection further used an adenovirus helper plasmid, pAdDeltaF6.
Figure 5:
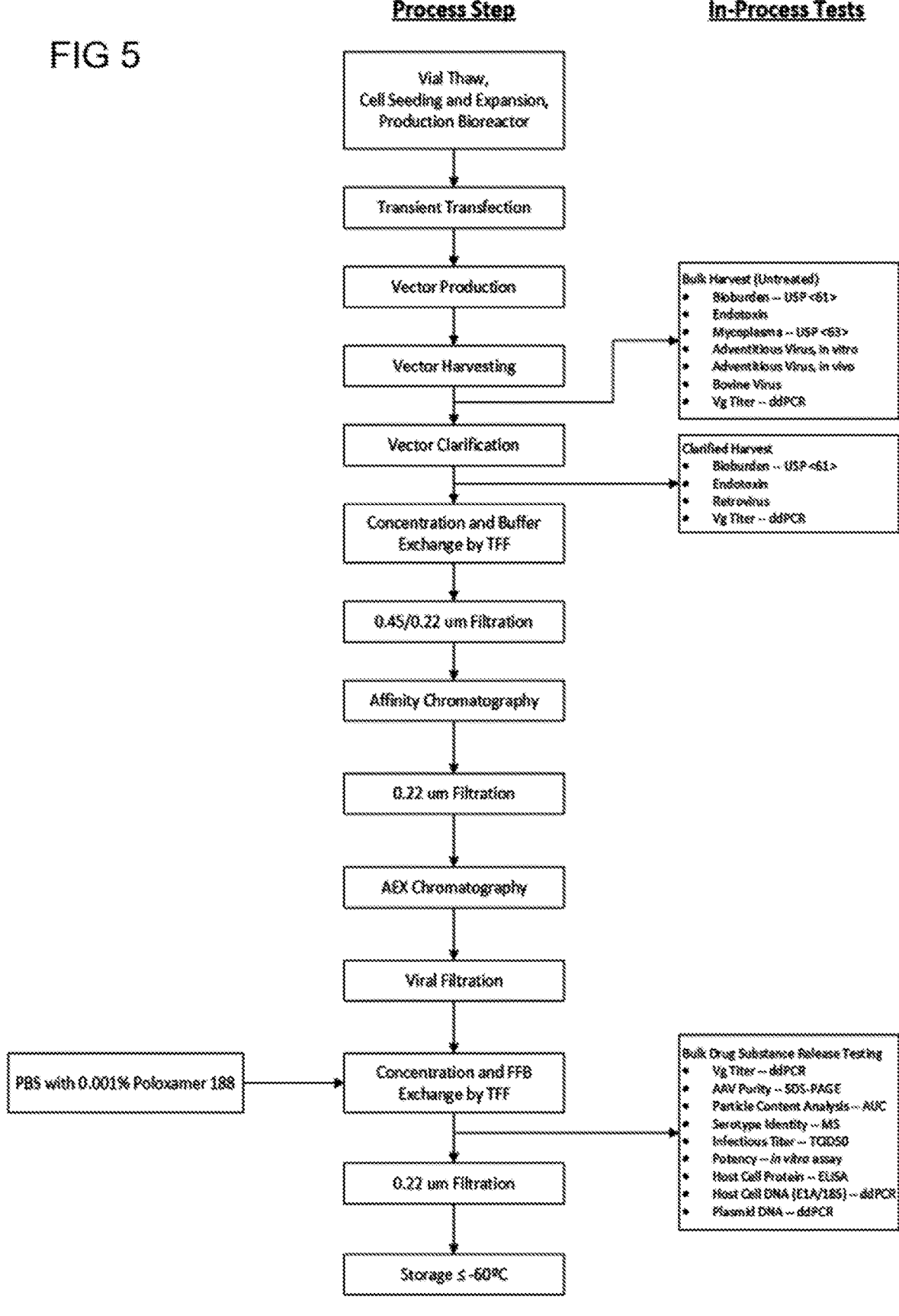
FIG. 5 is a flow chart for an rAAV manufacturing process using the engineered hu68M191 sequence to generate a recombinant AAV drug substance. Abbreviations: AAV=adeno-associated virus; AEX=anion exchange; AUC=analytical ultracentrifugation; ddPCR=droplet digital polymerase chain reaction; E1A=early region 1A (gene); ELISA=enzyme-linked immunosorbent assay; FFB=final formulation buffer; MS=mass spectrometry; PBS=phosphate-buffered saline; SDS-PAGE=sodium dodecyl sulfate polyacrylamide gel electrophoresis; TCID50=50% tissue culture infective dose; TFF=tangential flow filtration; USP=United States Pharmacopeia; Vg=vector genome.
Figure 6:
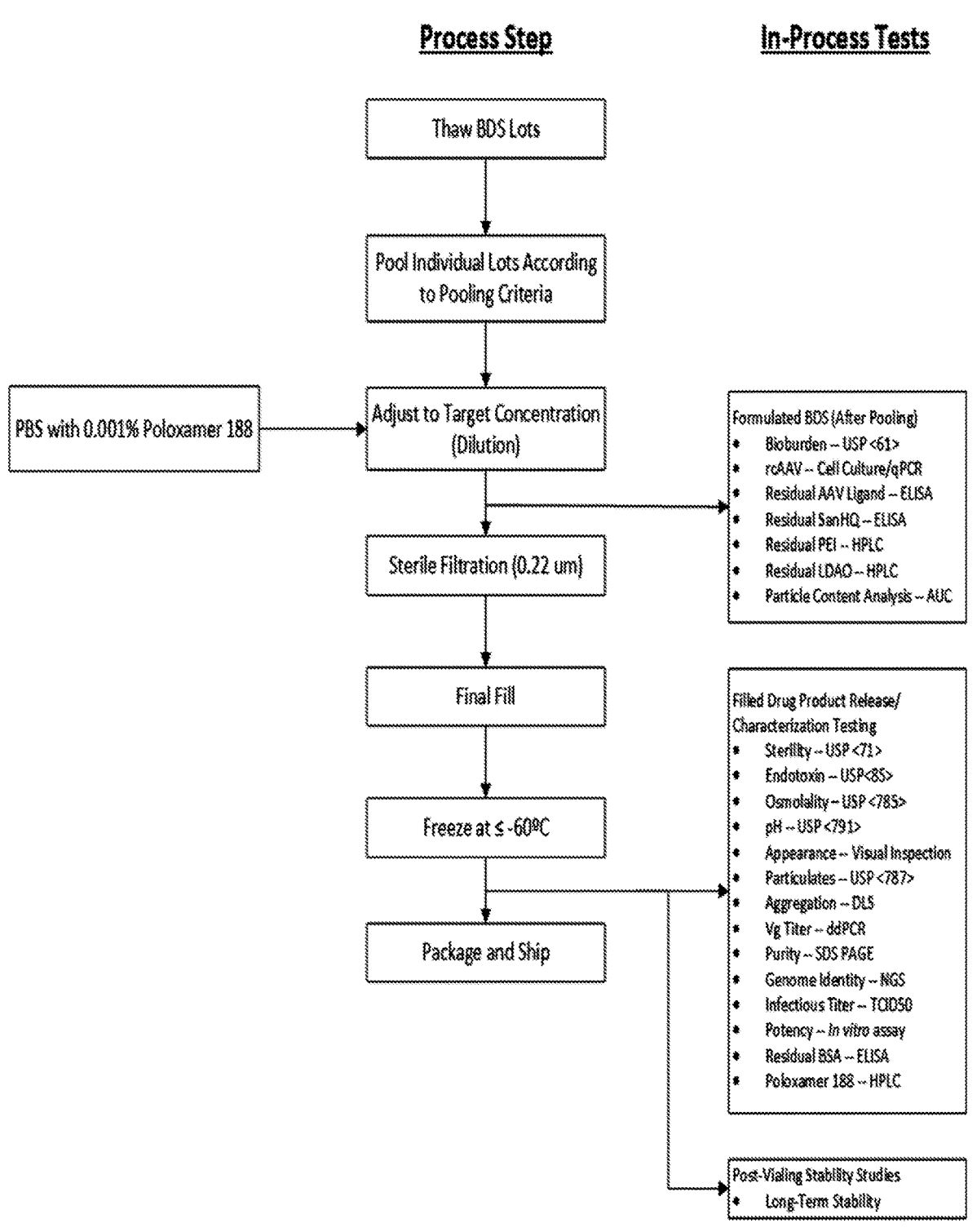
FIG. 6 is a flow chart for an rAAV manufacturing process. Abbreviations: AUC=analytical ultracentrifugation; BDS=bulk drug substance; BSA=bovine serum albumin; ddPCR=droplet digital polymerase chain reaction; E1A=early region 1A (gene); ELISA=enzyme-linked immunosorbent assay; NGS=next-generation sequencing; PBS=phosphate-buffered saline; qPCR=quantitative polymerase chain reaction; SDS-PAGE=sodium dodecyl sulfate polyacrylamide gel electrophoresis; TCID50=50% tissue culture infective dose; USP=United States Pharmacopeia; Vg=vector genome.

This resulted in ~30% yield increase at the 12-well plate production scale and more than 30% yield increase at single CellSTACK® production scale. The results from illustrative plates are shown in FIGS. 3A, 3B, and 4, respectively. (Sequence Listing Free Text)

The following information is provided for sequences containing free text under numeric identifier <223>.

| SEQ ID NO: (containing free text) | Free text under <223> |
|---|---|
| 1 | AAVhu68M191 |
| 2 | Synthetic Construct |
| 3 | AAV hu68 VP1 native |
| 4 | Synthetic Construct |
| 5 | AAVhu68 rep gene of *homo sapiens* origin |
| 6 | Synthetic Construct |
| 7 | AAV2 rep |
| 8 | Synthetic Construct |
| 9 | Spacer sequence |

All documents cited in this specification are incorporated herein by reference, as is U.S. Provisional Patent Application No. 63/093,275, filed Oct. 18, 2020. The Sequence Listing filed herewith, labelled "21-9487PCT_ST25.txt", and the sequences and text therein are incorporated by reference. While the invention has been described with reference to particular embodiments, it will be appreciated that modifications can be made without departing from the spirit of the invention. Such modifications are intended to fall within the scope of the appended claims.

The invention claimed is:

1. A production host cell for generating a recombinant adeno-associated virus (rAAV) having an AAVhu68 capsid comprising:

(a) a nucleic acid sequence of SEQ ID NO: 1 or a sequence at least 99% identical thereto encoding the AAVhu68 vp1 capsid protein operably linked to expression control sequences which direct expression of the AAVhu68 vp1 capsid protein in the host cell;

(b) a nucleic acid molecule for packaging into the AAVhu68 capsid, said nucleic acid molecule compris-ing at least one AAV inverted terminal repeat (ITR) and a non-AAV nucleic acid sequence encoding a gene product operably linked to sequences which direct expression of the product in a host cell; and (c) sufficient AAV rep functions and helper functions to permit packaging of the nucleic acid molecule into the AAVhu68 capsid.

2. The production host cell according to claim 1, wherein the host cell further comprises a nucleic acid sequence of about nucleotide 607 to about nucleotide 2211 of SEQ ID NO: 1 or a sequence at least 99% identical thereto encoding the AAVhu68 vp3 of about amino acid 203 to about amino acid 736 of SEQ ID NO: 2.

3. The production host cell according to claim 1, wherein the host cell is a human cell line or an insect cell line.

4. The production host cell according to claim 1, wherein the host cells is a HEK293 cell, HuH-7 cell, BHK cell, or Vero cell.

5. The production host cell according to claim 1, wherein the helper functions are provided by adenovirus, baculovirus, or herpes simplex virus proteins.

6. The production host cell according to claim 1, wherein the AAV rep is from a different AAV.

7. The production host cell according to claim 6, wherein the AAV rep is from AAV2.

8. The production host cell according to claim 1, wherein the AAV rep coding sequence and cap genes are on the same nucleic acid molecule, wherein there is optionally a spacer between the rep sequence and cap gene.

9. The production host cell according to claim 8, wherein the spacer is SEQ ID NO: 9.

10. The production host cell according to claim 1, wherein the AAV rep is AAVhu68rep characterized by the amino acid sequence of SEQ ID NO: 6, or a functional fragment thereof.

11. The production host cell according to claim 10, wherein the AAV rep is encoded by the nucleic acid sequence of SEQ ID NO: 5.

12. A suspension comprising production host cells according to claim 1.

13. The suspension according to claim 12, wherein the helper functions are herpes simplex virus helper functions.

14. The suspension according to claim 12, wherein the helper functions are baculovirus helper functions.

15. A cell culture comprising the production host cell according to claim 1.

16. The cell culture according to claim 15, wherein helper functions are adenovirus helper functions.

17. A substrate comprising an adherent cell line comprising the production host cell according to claim 1.

18. The suspension according to claim 12, wherein the host cells can produce an amount of rAAVhu68 particles that is at least 20% higher than the amount produced by AAVhu68 of SEQ ID NO: 3.

* * * * *

SEQUENCE LISTING

```
<160> NUMBER OF SEQ ID NOS: 9

<210> SEQ ID NO 1
<211> LENGTH: 2211
<212> TYPE: DNA
<213> ORGANISM: Artificial sequence
<220> FEATURE:
<223> OTHER INFORMATION: AAVhu68M191
<220> FEATURE:
<221> NAME/KEY: CDS
<222> LOCATION: (1)..(2211)

<400> SEQUENCE: 1 atg gct gcc gat ggt tat ctt cca gat tgg ctc gag gac aac ctc agt        48
Met Ala Ala Asp Gly Tyr Leu Pro Asp Trp Leu Glu Asp Asn Leu Ser
1               5                   10                  15 gaa ggc att cgc gag tgg tgg gct ttg aaa cct gga gcc cct caa ccc        96
Glu Gly Ile Arg Glu Trp Trp Ala Leu Lys Pro Gly Ala Pro Gln Pro
            20                  25                  30 aag gca aat caa caa cat caa gac aac gct cgg ggt ctt gtg ctt ccg       144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg       192
Gly Tyr Lys Tyr Leu Gly Pro Gly Asn Gly Leu Asp Lys Gly Glu Pro
    50                  55                  60 gtc aac gaa gca gac gcg gcg gcc ctc gag cac gac aag gcc tac gac       240
Val Asn Glu Ala Asp Ala Ala Ala Leu Glu His Asp Lys Ala Tyr Asp
65                  70                  75                  80 cag cag ctc aag gcc gga gac aac ccg tac ctc aag tac aac cac gcc       288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc       336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct       384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg       432
Leu Gly Leu Val Glu Glu Ala Ala Lys Thr Ala Pro Gly Lys Lys Arg
```

-continued

```
            130               135               140 cct gta gag cag tct cct cag gaa ccg gac tcc tcc gtg ggt att ggc      480
Pro Val Glu Gln Ser Pro Gln Glu Pro Asp Ser Ser Val Gly Ile Gly
145               150               155               160 aaa tcg ggt gca cag ccc gct aaa aag aga ctc aat ttc ggt cag act      528
Lys Ser Gly Ala Gln Pro Ala Lys Lys Arg Leu Asn Phe Gly Gln Thr
                  165               170               175 ggc gac aca gag tca gtc ccc gac cct caa cca atc gga gaa cct ccc      576
Gly Asp Thr Glu Ser Val Pro Asp Pro Gln Pro Ile Gly Glu Pro Pro
            180               185               190 gca gcc ccc tca ggt gtg gga tct ctt aca atg gct tca ggt ggt ggc      624
Ala Ala Pro Ser Gly Val Gly Ser Leu Thr Met Ala Ser Gly Gly Gly
            195               200               205 gca cca gtg gca gac aat aac gaa ggt gcc gat gga gtg ggt agt tcc      672
Ala Pro Val Ala Asp Asn Asn Glu Gly Ala Asp Gly Val Gly Ser Ser
      210               215               220 tcg gga aat tgg cat tgc gat tcc caa tgg ctg ggg gac aga gtc atc      720
Ser Gly Asn Trp His Cys Asp Ser Gln Trp Leu Gly Asp Arg Val Ile
225               230               235               240 acc acc agc acc cga acc tgg gcc ctg ccc acc tac aac aat cac ctc      768
Thr Thr Ser Thr Arg Thr Trp Ala Leu Pro Thr Tyr Asn Asn His Leu
                  245               250               255 tac aag caa atc tcc aac agc aca tct gga gga tct tca aat gac aac      816
Tyr Lys Gln Ile Ser Asn Ser Thr Ser Gly Gly Ser Ser Asn Asp Asn
                  260               265               270 gcc tac ttc ggc tac agc acc ccc tgg ggg tat ttt gac ttc aac aga      864
Ala Tyr Phe Gly Tyr Ser Thr Pro Trp Gly Tyr Phe Asp Phe Asn Arg
            275               280               285 ttc cac tgc cac ttc tca cca cgt gac tgg caa aga ctc atc aac aac      912
Phe His Cys His Phe Ser Pro Arg Asp Trp Gln Arg Leu Ile Asn Asn
      290               295               300 aac tgg gga ttc cgg cct aag cga ctc aac ttc aag ctc ttc aac att      960
Asn Trp Gly Phe Arg Pro Lys Arg Leu Asn Phe Lys Leu Phe Asn Ile
305               310               315               320 cag gtc aaa gag gtt acg gac aac aat gga gtc aag acc atc gct aat     1008
Gln Val Lys Glu Val Thr Asp Asn Asn Gly Val Lys Thr Ile Ala Asn
                  325               330               335 aac ctt acc agc acg gtc cag gtc ttc acg gac tca gac tat cag ctc     1056
Asn Leu Thr Ser Thr Val Gln Val Phe Thr Asp Ser Asp Tyr Gln Leu
                  340               345               350 ccg tac gtg ctc ggg tcg gct cac gag ggc tgc ctc ccg ccg ttc cca     1104
Pro Tyr Val Leu Gly Ser Ala His Glu Gly Cys Leu Pro Pro Phe Pro
            355               360               365 gcg gac gtt ttc atg att cct cag tat gga tac ctc acc ctg aac gac     1152
Ala Asp Val Phe Met Ile Pro Gln Tyr Gly Tyr Leu Thr Leu Asn Asp
      370               375               380 ggc agt cag gcg gtg ggc cgc tca tcc ttc tac tgc ctg gag tac ttc     1200
Gly Ser Gln Ala Val Gly Arg Ser Ser Phe Tyr Cys Leu Glu Tyr Phe
385               390               395               400 cct tcg cag atg ctg agg act ggc aac aac ttc cag ttc agc tac gag     1248
Pro Ser Gln Met Leu Arg Thr Gly Asn Asn Phe Gln Phe Ser Tyr Glu
                  405               410               415 ttc gag aac gtc cct ttc cac agc agc tac gcc cac agc cag agt ttg     1296
Phe Glu Asn Val Pro Phe His Ser Ser Tyr Ala His Ser Gln Ser Leu
                  420               425               430 gac cgc ttg atg aac cct ctg atc gac cag tac ctg tac tac ctg tca     1344
Asp Arg Leu Met Asn Pro Leu Ile Asp Gln Tyr Leu Tyr Tyr Leu Ser
            435               440               445 aag acg atc aac ggt tct ggc cag aac cag cag acg ctg aag ttc agc     1392
```

-continued

```
Lys Thr Ile Asn Gly Ser Gly Gln Asn Gln Gln Thr Leu Lys Phe Ser
    450             455                 460 gtg gcc ggg cct agc aac atg gcc gtc cag ggc aga aac tac atc cct      1440
Val Ala Gly Pro Ser Asn Met Ala Val Gln Gly Arg Asn Tyr Ile Pro
465             470                 475                 480 ggg ccc agc tac cgg cag cag aga gtc tca acc act gtg act cag aac      1488
Gly Pro Ser Tyr Arg Gln Gln Arg Val Ser Thr Thr Val Thr Gln Asn
                485                 490                 495 aac aac agt gag ttc gcc tgg cct ggc gcc agc tct tgg gcc ctc aac      1536
Asn Asn Ser Glu Phe Ala Trp Pro Gly Ala Ser Ser Trp Ala Leu Asn
            500                 505                 510 ggc cgc aac tcg ctg atg aac cca ggc cca gcc atg gcc agt cac aag      1584
Gly Arg Asn Ser Leu Met Asn Pro Gly Pro Ala Met Ala Ser His Lys
        515                 520                 525 gag ggc gag gac cgt ttc ttc cct ttg tct ggc tct ctg atc ttc ggc      1632
Glu Gly Glu Asp Arg Phe Phe Pro Leu Ser Gly Ser Leu Ile Phe Gly
    530                 535                 540 aag cag ggg acc ggc aga gac aac gtg gac gcg gac aag gtc atg atc      1680
Lys Gln Gly Thr Gly Arg Asp Asn Val Asp Ala Asp Lys Val Met Ile
545                 550                 555                 560 acg aac gag gag gag atc aag acc acc aac cct gtg gca acc gag tcc      1728
Thr Asn Glu Glu Glu Ile Lys Thr Thr Asn Pro Val Ala Thr Glu Ser
                565                 570                 575 tac ggc cag gtg gca acc aac cac cag agc gcc cag gca cag gcg cag      1776
Tyr Gly Gln Val Ala Thr Asn His Gln Ser Ala Gln Ala Gln Ala Gln
                580                 585                 590 act ggc tgg gtc cag aac cag ggg atc ctg cct ggc atg gtg tgg cag      1824
Thr Gly Trp Val Gln Asn Gln Gly Ile Leu Pro Gly Met Val Trp Gln
            595                 600                 605 gac cgt gac gtg tac ctg cag ggc cct atc tgg gca aag atc cct cac      1872
Asp Arg Asp Val Tyr Leu Gln Gly Pro Ile Trp Ala Lys Ile Pro His
    610                 615                 620 acg gac ggc aac ttc cac cct tct cct ctg atg ggc ggc ttc ggc atg      1920
Thr Asp Gly Asn Phe His Pro Ser Pro Leu Met Gly Gly Phe Gly Met
625                 630                 635                 640 aag cac ccg cct cct cag atc ctc atc aag aac act ccg gtc ccg gca      1968
Lys His Pro Pro Pro Gln Ile Leu Ile Lys Asn Thr Pro Val Pro Ala
                645                 650                 655 gac cct ccg acg gcc ttc aac aag gac aag ctg aac tca ttc atc act      2016
Asp Pro Pro Thr Ala Phe Asn Lys Asp Lys Leu Asn Ser Phe Ile Thr
                660                 665                 670 cag tac tcc act ggc cag gtc agc gtg gag atc gag tgg gag ctg cag      2064
Gln Tyr Ser Thr Gly Gln Val Ser Val Glu Ile Glu Trp Glu Leu Gln
            675                 680                 685 aag gag aac agc aag cgt tgg aac cca gag atc cag tac act tcc aac      2112
Lys Glu Asn Ser Lys Arg Trp Asn Pro Glu Ile Gln Tyr Thr Ser Asn
        690                 695                 700 tac tac aag tct aac aac gtg gag ttc gcc gtc aac act gag ggt gtg      2160
Tyr Tyr Lys Ser Asn Asn Val Glu Phe Ala Val Asn Thr Glu Gly Val
705                 710                 715                 720 tac agt gag cct cgc cct atc ggc acc cgg tac ctc acc cga aac ttg      2208
Tyr Ser Glu Pro Arg Pro Ile Gly Thr Arg Tyr Leu Thr Arg Asn Leu
                725                 730                 735 tga                                                                   2211
```

<210> SEQ ID NO 2
<211> LENGTH: 736
<212> TYPE: PRT
<213> ORGANISM: Artificial sequence
<220> FEATURE:

<223> OTHER INFORMATION: Synthetic Construct

<400> SEQUENCE: 2

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Val Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400
```

-continued

```
Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

```
<210> SEQ ID NO 3
<211> LENGTH: 2211
<212> TYPE: DNA
<213> ORGANISM: Artificial sequence
<220> FEATURE:
<223> OTHER INFORMATION: AAV hu68 VP1 native
<220> FEATURE:
<221> NAME/KEY: CDS
<222> LOCATION: (1)..(2211)

<400> SEQUENCE: 3 atg gct gcc gat ggt tat ctt cca gat tgg ctc gag gac aac ctc agt      48
Met Ala Ala Asp Gly Tyr Leu Pro Asp Trp Leu Glu Asp Asn Leu Ser
1               5                   10                  15
```

-continued

```
gaa ggc att cgc gag tgg tgg gct ttg aaa cct gga gcc cct caa ccc          96
Glu Gly Ile Arg Glu Trp Trp Ala Leu Lys Pro Gly Ala Pro Gln Pro
         20              25              30 aag gca aat caa caa cat caa gac aac gct cgg ggt ctt gtg ctt ccg         144
Lys Ala Asn Gln Gln His Gln Asp Asn Ala Arg Gly Leu Val Leu Pro
     35              40              45 ggt tac aaa tac ctt gga ccc ggc aac gga ctc gac aag ggg gag ccg         192
Gly Tyr Lys Tyr Leu Gly Pro Gly Asn Gly Leu Asp Lys Gly Glu Pro
     50              55              60 gtc aac gaa gca gac gcg gcg gcc ctc gag cac gac aag gcc tac gac         240
Val Asn Glu Ala Asp Ala Ala Ala Leu Glu His Asp Lys Ala Tyr Asp
65              70              75              80 cag cag ctc aag gcc gga gac aac ccg tac ctc aag tac aac cac gcc         288
Gln Gln Leu Lys Ala Gly Asp Asn Pro Tyr Leu Lys Tyr Asn His Ala
             85              90              95 gac gcc gag ttc cag gag cgg ctc aaa gaa gat acg tct ttt ggg ggc         336
Asp Ala Glu Phe Gln Glu Arg Leu Lys Glu Asp Thr Ser Phe Gly Gly
             100             105             110 aac ctc ggg cga gca gtc ttc cag gcc aaa aag agg ctt ctt gaa cct         384
Asn Leu Gly Arg Ala Val Phe Gln Ala Lys Lys Arg Leu Leu Glu Pro
         115             120             125 ctt ggt ctg gtt gag gaa gcg gct aag acg gct cct gga aag aag agg         432
Leu Gly Leu Val Glu Glu Ala Ala Lys Thr Ala Pro Gly Lys Lys Arg
     130             135             140 cct gta gag cag tct cct cag gaa ccg gac tcc tcc gtg ggt att ggc         480
Pro Val Glu Gln Ser Pro Gln Glu Pro Asp Ser Ser Val Gly Ile Gly
145             150             155             160 aaa tcg ggt gca cag ccc gct aaa aag aga ctc aat ttc ggt cag act         528
Lys Ser Gly Ala Gln Pro Ala Lys Lys Arg Leu Asn Phe Gly Gln Thr
             165             170             175 ggc gac aca gag tca gtc ccc gac cct caa cca atc gga gaa cct ccc         576
Gly Asp Thr Glu Ser Val Pro Asp Pro Gln Pro Ile Gly Glu Pro Pro
             180             185             190 gca gcc ccc tca ggt gtg gga tct ctt aca atg gct tca ggt ggt ggc         624
Ala Ala Pro Ser Gly Val Gly Ser Leu Thr Met Ala Ser Gly Gly Gly
         195             200             205 gca cca gtg gca gac aat aac gaa ggt gcc gat gga gtg ggt agt tcc         672
Ala Pro Val Ala Asp Asn Asn Glu Gly Ala Asp Gly Val Gly Ser Ser
     210             215             220 tcg gga aat tgg cat tgc gat tcc caa tgg ctg ggg gac aga gtc atc         720
Ser Gly Asn Trp His Cys Asp Ser Gln Trp Leu Gly Asp Arg Val Ile
225             230             235             240 acc acc agc acc cga acc tgg gcc ctg ccc acc tac aac aat cac ctc         768
Thr Thr Ser Thr Arg Thr Trp Ala Leu Pro Thr Tyr Asn Asn His Leu
             245             250             255 tac aag caa atc tcc aac agc aca tct gga gga tct tca aat gac aac         816
Tyr Lys Gln Ile Ser Asn Ser Thr Ser Gly Gly Ser Ser Asn Asp Asn
             260             265             270 gcc tac ttc ggc tac agc acc ccc tgg ggg tat ttt gac ttc aac aga         864
Ala Tyr Phe Gly Tyr Ser Thr Pro Trp Gly Tyr Phe Asp Phe Asn Arg
         275             280             285 ttc cac tgc cac ttc tca cca cgt gac tgg caa aga ctc atc aac aac         912
Phe His Cys His Phe Ser Pro Arg Asp Trp Gln Arg Leu Ile Asn Asn
         290             295             300 aac tgg gga ttc cgg cct aag cga ctc aac ttc aag ctc ttc aac att         960
Asn Trp Gly Phe Arg Pro Lys Arg Leu Asn Phe Lys Leu Phe Asn Ile
305             310             315             320 cag gtc aaa gag gtt acg gac aac aat gga gtc aag acc atc gct aat        1008
Gln Val Lys Glu Val Thr Asp Asn Asn Gly Val Lys Thr Ile Ala Asn
```

-continued

```
                325                 330                 335 aac ctt acc agc acg gtc cag gtc ttc acg gac tca gac tat cag ctc    1056
Asn Leu Thr Ser Thr Val Gln Val Phe Thr Asp Ser Asp Tyr Gln Leu
        340                 345                 350 ccg tac gtg ctc ggg tcg gct cac gag ggc tgc ctc ccg ccg ttc cca    1104
Pro Tyr Val Leu Gly Ser Ala His Glu Gly Cys Leu Pro Pro Phe Pro
        355                 360                 365 gcg gac gtt ttc atg att cct cag tac ggg tat cta acg ctt aat gat    1152
Ala Asp Val Phe Met Ile Pro Gln Tyr Gly Tyr Leu Thr Leu Asn Asp
        370                 375                 380 gga agc caa gcc gtg ggt cgt tcg tcc ttt tac tgc ctg gaa tat ttc    1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag    1248
Pro Ser Gln Met Leu Arg Thr Gly Asn Asn Phe Gln Phe Ser Tyr Glu
                405                 410                 415 ttt gag aac gta cct ttc cat agc agc tat gct cac agc caa agc ctg    1296
Phe Glu Asn Val Pro Phe His Ser Ser Tyr Ala His Ser Gln Ser Leu
            420                 425                 430 gac cga ctc atg aat cca ctc atc gac caa tac ttg tac tat ctc tca    1344
Asp Arg Leu Met Asn Pro Leu Ile Asp Gln Tyr Leu Tyr Tyr Leu Ser
            435                 440                 445 aag act att aac ggt tct gga cag aat caa caa acg cta aaa ttc agt    1392
Lys Thr Ile Asn Gly Ser Gly Gln Asn Gln Gln Thr Leu Lys Phe Ser
            450                 455                 460 gtg gcc gga ccc agc aac atg gct gtc cag gga aga aac tac ata cct    1440
Val Ala Gly Pro Ser Asn Met Ala Val Gln Gly Arg Asn Tyr Ile Pro
465                 470                 475                 480 gga ccc agc tac cga caa caa cgt gtc tca acc act gtg act caa aac    1488
Gly Pro Ser Tyr Arg Gln Gln Arg Val Ser Thr Thr Val Thr Gln Asn
                485                 490                 495 aac aac agc gaa ttt gct tgg cct gga gct tct tct tgg gct ctc aat    1536
Asn Asn Ser Glu Phe Ala Trp Pro Gly Ala Ser Ser Trp Ala Leu Asn
            500                 505                 510 gga cgt aat agc ttg atg aat cct gga cct gct atg gcc agc cac aaa    1584
Gly Arg Asn Ser Leu Met Asn Pro Gly Pro Ala Met Ala Ser His Lys
            515                 520                 525 gaa gga gag gac cgt ttc ttt cct ttg tct gga tct tta att ttt ggc    1632
Glu Gly Glu Asp Arg Phe Phe Pro Leu Ser Gly Ser Leu Ile Phe Gly
            530                 535                 540 aaa caa gga act gga aga gac aac gtg gat gcg gac aaa gtc atg ata    1680
Lys Gln Gly Thr Gly Arg Asp Asn Val Asp Ala Asp Lys Val Met Ile
545                 550                 555                 560 acc aac gaa gaa gaa att aaa act acc aac cca gta gca acg gag tcc    1728
Thr Asn Glu Glu Glu Ile Lys Thr Thr Asn Pro Val Ala Thr Glu Ser
                565                 570                 575 tat gga caa gtg gcc aca aac cac cag agt gcc caa gca cag gcg cag    1776
Tyr Gly Gln Val Ala Thr Asn His Gln Ser Ala Gln Ala Gln Ala Gln
            580                 585                 590 acc ggc tgg gtt caa aac caa gga ata ctt ccg ggt atg gtt tgg cag    1824
Thr Gly Trp Val Gln Asn Gln Gly Ile Leu Pro Gly Met Val Trp Gln
            595                 600                 605 gac aga gat gtg tac ctg caa gga ccc att tgg gcc aaa att cct cac    1872
Asp Arg Asp Val Tyr Leu Gln Gly Pro Ile Trp Ala Lys Ile Pro His
            610                 615                 620 acg gac ggc aac ttt cac cct tct ccg ctg atg gga ggg ttt gga atg    1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg    1968
```

-continued

```
Lys His Pro Pro Pro Gln Ile Leu Ile Lys Asn Thr Pro Val Pro Ala
                645              650              655 gat cct cca acg gct ttc aac aag gac aag ctg aac tct ttc atc acc      2016
Asp Pro Pro Thr Ala Phe Asn Lys Asp Lys Leu Asn Ser Phe Ile Thr
            660              665              670 cag tat tct act ggc caa gtc agc gtg gag att gag tgg gag ctg cag      2064
Gln Tyr Ser Thr Gly Gln Val Ser Val Glu Ile Glu Trp Glu Leu Gln
            675              680              685 aag gaa aac agc aag cgc tgg aac ccg gag atc cag tac act tcc aac      2112
Lys Glu Asn Ser Lys Arg Trp Asn Pro Glu Ile Gln Tyr Thr Ser Asn
        690              695              700 tat tac aag tct aat aat gtt gaa ttt gct gtt aat act gaa ggt gtt      2160
Tyr Tyr Lys Ser Asn Asn Val Glu Phe Ala Val Asn Thr Glu Gly Val
705              710              715              720 tat tct gaa ccc cgc ccc att ggc acc aga tac ctg act cgt aat ctg      2208
Tyr Ser Glu Pro Arg Pro Ile Gly Thr Arg Tyr Leu Thr Arg Asn Leu
            725              730              735 taa                                                                  2211
```

```
<210> SEQ ID NO 4
<211> LENGTH: 736
<212> TYPE: PRT
<213> ORGANISM: Artificial sequence
<220> FEATURE:
<223> OTHER INFORMATION: Synthetic Construct

<400> SEQUENCE: 4

Met Ala Ala Asp Gly Tyr Leu Pro Asp Trp Leu Glu Asp Asn Leu Ser
1               5               10              15

Glu Gly Ile Arg Glu Trp Trp Ala Leu Lys Pro Gly Ala Pro Gln Pro
            20              25              30

Lys Ala Asn Gln Gln His Gln Asp Asn Ala Arg Gly Leu Val Leu Pro
        35              40              45

Gly Tyr Lys Tyr Leu Gly Pro Gly Asn Gly Leu Asp Lys Gly Glu Pro
    50              55              60

Val Asn Glu Ala Asp Ala Ala Ala Leu Glu His Asp Lys Ala Tyr Asp
65              70              75              80

Gln Gln Leu Lys Ala Gly Asp Asn Pro Tyr Leu Lys Tyr Asn His Ala
            85              90              95

Asp Ala Glu Phe Gln Glu Arg Leu Lys Glu Asp Thr Ser Phe Gly Gly
            100             105             110

Asn Leu Gly Arg Ala Val Phe Gln Ala Lys Lys Arg Leu Leu Glu Pro
        115             120             125

Leu Gly Leu Val Glu Glu Ala Ala Lys Thr Ala Pro Gly Lys Lys Arg
    130             135             140

Pro Val Glu Gln Ser Pro Gln Glu Pro Asp Ser Ser Val Gly Ile Gly
145             150             155             160

Lys Ser Gly Ala Gln Pro Ala Lys Lys Arg Leu Asn Phe Gly Gln Thr
            165             170             175

Gly Asp Thr Glu Ser Val Pro Asp Pro Gln Pro Ile Gly Glu Pro Pro
            180             185             190

Ala Ala Pro Ser Gly Val Gly Ser Leu Thr Met Ala Ser Gly Gly Gly
        195             200             205

Ala Pro Val Ala Asp Asn Asn Glu Gly Ala Asp Gly Val Gly Ser Ser
    210             215             220

Ser Gly Asn Trp His Cys Asp Ser Gln Trp Leu Gly Asp Arg Val Ile
225             230             235             240
```

-continued

```
Thr Thr Ser Thr Arg Thr Trp Ala Leu Pro Thr Tyr Asn Asn His Leu
            245             250                 255

Tyr Lys Gln Ile Ser Asn Ser Thr Ser Gly Gly Ser Ser Asn Asp Asn
            260             265                 270

Ala Tyr Phe Gly Tyr Ser Thr Pro Trp Gly Tyr Phe Asp Phe Asn Arg
            275             280                 285

Phe His Cys His Phe Ser Pro Arg Asp Trp Gln Arg Leu Ile Asn Asn
            290             295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655
```

-continued

```
Asp Pro Pro Thr Ala Phe Asn Lys Asp Lys Leu Asn Ser Phe Ile Thr
            660             665                 670

Gln Tyr Ser Thr Gly Gln Val Ser Val Glu Ile Glu Trp Glu Leu Gln
        675                 680             685

Lys Glu Asn Ser Lys Arg Trp Asn Pro Glu Ile Gln Tyr Thr Ser Asn
        690             695             700

Tyr Tyr Lys Ser Asn Asn Val Glu Phe Ala Val Asn Thr Glu Gly Val
705             710             715             720

Tyr Ser Glu Pro Arg Pro Ile Gly Thr Arg Tyr Leu Thr Arg Asn Leu
            725             730             735

<210> SEQ ID NO 5
<211> LENGTH: 1866
<212> TYPE: DNA
<213> ORGANISM: Artificial Sequence
<220> FEATURE:
<223> OTHER INFORMATION: AAVhu68 rep gene of homo sapiens origin
<220> FEATURE:
<221> NAME/KEY: CDS
<222> LOCATION: (1)..(1866)

<400> SEQUENCE: 5 atg ccg ggg ttt tac gag att gtg att aag gtc ccc agc gac ctt gac        48
Met Pro Gly Phe Tyr Glu Ile Val Ile Lys Val Pro Ser Asp Leu Asp
1               5                   10                  15 gag cat ctg ccc ggc att tct gac agc ttt gtg aac tgg gtg gcc gag        96
Glu His Leu Pro Gly Ile Ser Asp Ser Phe Val Asn Trp Val Ala Glu
            20                  25                  30 aag gaa tgg gag ttg ccg cca gat tct gac atg gat ctg aat ctg att       144
Lys Glu Trp Glu Leu Pro Pro Asp Ser Asp Met Asp Leu Asn Leu Ile
        35                  40                  45 gag cag gca ccc ctg acc gtg gcc gag aag ctg cag cgc gac ttt ctg       192
Glu Gln Ala Pro Leu Thr Val Ala Glu Lys Leu Gln Arg Asp Phe Leu
        50                  55                  60 acg gaa tgg cgc cgt gtg agt aag gcc ccg gag gct ctt ttc ttt gtg       240
Thr Glu Trp Arg Arg Val Ser Lys Ala Pro Glu Ala Leu Phe Phe Val
65                  70                  75                  80 caa ttt gag aag gga gag agc tac ttc cac atg cac gtg ctc gtg gaa       288
Gln Phe Glu Lys Gly Glu Ser Tyr Phe His Met His Val Leu Val Glu
                85                  90                  95 acc acc ggg gtg aaa tcc atg gtt ttg gga cgt ttc ctg agt cag att       336
Thr Thr Gly Val Lys Ser Met Val Leu Gly Arg Phe Leu Ser Gln Ile
            100                 105                 110 cgc gaa aaa ctg att cag aga att tac cgc ggg atc gag ccg act ttg       384
Arg Glu Lys Leu Ile Gln Arg Ile Tyr Arg Gly Ile Glu Pro Thr Leu
        115                 120                 125 cca aac tgg ttc gcg gtc aca aag acc aga aat ggc gcc gga ggc ggg       432
Pro Asn Trp Phe Ala Val Thr Lys Thr Arg Asn Gly Ala Gly Gly Gly
        130                 135                 140 aac aag gtg gtg gat gag tgc tac atc ccc aat tac ttg ctc ccc aaa       480
Asn Lys Val Val Asp Glu Cys Tyr Ile Pro Asn Tyr Leu Leu Pro Lys
145                 150                 155                 160 acc cag cct gag ctc cag tgg gcg tgg act aat atg gaa cag tat tta       528
Thr Gln Pro Glu Leu Gln Trp Ala Trp Thr Asn Met Glu Gln Tyr Leu
                165                 170                 175 agc gcc tgt ttg aat ctc acg gag cgt aaa cgg ttg gtg gcg cag cat       576
Ser Ala Cys Leu Asn Leu Thr Glu Arg Lys Arg Leu Val Ala Gln His
            180                 185                 190 ctg acg cac gtg tcg cag acg cag gag cag aac aaa gag aat cag aat       624
Leu Thr His Val Ser Gln Thr Gln Glu Gln Asn Lys Glu Asn Gln Asn
        195                 200                 205
```

-continued

```
ccc aat tct gat gcg ccg gtg atc aga tca aaa act tca gcc agg tac      672
Pro Asn Ser Asp Ala Pro Val Ile Arg Ser Lys Thr Ser Ala Arg Tyr
    210             215             220 atg gag ctg gtc ggg tgg ctc gtg gac aag ggg att acc tcg gag aag      720
Met Glu Leu Val Gly Trp Leu Val Asp Lys Gly Ile Thr Ser Glu Lys
225             230             235             240 cag tgg atc cag gag gac cag gcc tca tac atc tcc ttc aat gcg gcc      768
Gln Trp Ile Gln Glu Asp Gln Ala Ser Tyr Ile Ser Phe Asn Ala Ala
                245             250             255 tcc aac tcg cgg tcc caa atc aag gtc gcc ttg gac aat gcg gga aag      816
Ser Asn Ser Arg Ser Gln Ile Lys Val Ala Leu Asp Asn Ala Gly Lys
                260             265             270 att atg agc ctg act aaa acc gcc ccc gac tac ctg gtg ggc cag cag      864
Ile Met Ser Leu Thr Lys Thr Ala Pro Asp Tyr Leu Val Gly Gln Gln
            275             280             285 ccc gtg gag gac att tcc agc aat cgg att tat aaa att ttg gaa cta      912
Pro Val Glu Asp Ile Ser Ser Asn Arg Ile Tyr Lys Ile Leu Glu Leu
    290             295             300 aac ggg tac gat ccc caa tat gcg gct tcc gtc ttt ctg gga tgg gcc      960
Asn Gly Tyr Asp Pro Gln Tyr Ala Ala Ser Val Phe Leu Gly Trp Ala
305             310             315             320 acg aaa aag ttc ggc aag agg aac acc atc tgg ctg ttt ggg cct gca     1008
Thr Lys Lys Phe Gly Lys Arg Asn Thr Ile Trp Leu Phe Gly Pro Ala
                325             330             335 act acc ggg aag acc aac atc gcg gag gcc ata gcc cac act gtg ccc     1056
Thr Thr Gly Lys Thr Asn Ile Ala Glu Ala Ile Ala His Thr Val Pro
                340             345             350 ttc tac ggg tgc gta aac tgg acc aat gag aac ttt ccc ttc aac gac     1104
Phe Tyr Gly Cys Val Asn Trp Thr Asn Glu Asn Phe Pro Phe Asn Asp
            355             360             365 tgt gtc gac aag atg gtg atc tgg tgg gag gag ggg aag atg acc gcc     1152
Cys Val Asp Lys Met Val Ile Trp Trp Glu Glu Gly Lys Met Thr Ala
    370             375             380 aag gtc gtg gag tcg gcc aaa gcc att ctc gga gga agc aag gtg cgc     1200
Lys Val Val Glu Ser Ala Lys Ala Ile Leu Gly Gly Ser Lys Val Arg
385             390             395             400 gtg gac cag aaa tgc aag tcc tcg gcc cag ata gac ccg act ccc gtg     1248
Val Asp Gln Lys Cys Lys Ser Ser Ala Gln Ile Asp Pro Thr Pro Val
                405             410             415 atc gtc acc tcc aac acc aac atg tgc gcc gtg att gac ggg aac tca     1296
Ile Val Thr Ser Asn Thr Asn Met Cys Ala Val Ile Asp Gly Asn Ser
                420             425             430 acg acc ttc gaa cac cag cag ccg ttg caa gac cgg atg ttc aaa ttt     1344
Thr Thr Phe Glu His Gln Gln Pro Leu Gln Asp Arg Met Phe Lys Phe
            435             440             445 gaa ctc acc cgc cgt ctg gat cat gac ttt ggg aag gtc acc aag cag     1392
Glu Leu Thr Arg Arg Leu Asp His Asp Phe Gly Lys Val Thr Lys Gln
    450             455             460 gaa gtc aaa gac ttt ttc cgg tgg gca aag gat cac gtg gtt gag gtg     1440
Glu Val Lys Asp Phe Phe Arg Trp Ala Lys Asp His Val Val Glu Val
465             470             475             480 gag cat gaa ttc tac gtc aaa aag ggt gga gcc aag aaa aga ccc gcc     1488
Glu His Glu Phe Tyr Val Lys Lys Gly Gly Ala Lys Lys Arg Pro Ala
                485             490             495 ccc agt gac gca gat ata agt gag ccc aaa cgg gtg cgc gag tca gtt     1536
Pro Ser Asp Ala Asp Ile Ser Glu Pro Lys Arg Val Arg Glu Ser Val
                500             505             510 gcg cag cca tcg acg tca gac gcg gaa gct tcg atc aac tac gcg gac     1584
Ala Gln Pro Ser Thr Ser Asp Ala Glu Ala Ser Ile Asn Tyr Ala Asp
```

-continued

```
            515                    520                    525 agg tac caa aac aaa tgt tct cgt cac gtg ggc atg aat ctg atg ctg        1632
Arg Tyr Gln Asn Lys Cys Ser Arg His Val Gly Met Asn Leu Met Leu
    530                    535                    540 ttt ccc tgc aga caa tgc gag aga ctg aat cag aat tca aat atc tgc        1680
Phe Pro Cys Arg Gln Cys Glu Arg Leu Asn Gln Asn Ser Asn Ile Cys
545                    550                    555                    560 ttc act cac ggt gtc aaa gac tgt tta gag tgc ttt ccc gtg tca gaa        1728
Phe Thr His Gly Val Lys Asp Cys Leu Glu Cys Phe Pro Val Ser Glu
                565                    570                    575 tct caa ccc gtt tct gtc gtc aaa aag gcg tat cag aaa ctg tgc tac        1776
Ser Gln Pro Val Ser Val Val Lys Lys Ala Tyr Gln Lys Leu Cys Tyr
                580                    585                    590 att cat cac atc atg gga aag gtg cca gac gct tgc act gct tgc gac        1824
Ile His His Ile Met Gly Lys Val Pro Asp Ala Cys Thr Ala Cys Asp
            595                    600                    605 ctg gtc aat gtg gac ttg gat gac tgt gtt tct gaa caa taa               1866
Leu Val Asn Val Asp Leu Asp Asp Cys Val Ser Glu Gln
    610                    615                    620

<210> SEQ ID NO 6
<211> LENGTH: 621
<212> TYPE: PRT
<213> ORGANISM: Artificial Sequence
<220> FEATURE:
<223> OTHER INFORMATION: Synthetic Construct

<400> SEQUENCE: 6

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
            130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
                180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
```

-continued

```
225                230                235                240

Gln Trp Ile Gln Glu Asp Gln Ala Ser Tyr Ile Ser Phe Asn Ala Ala
                245                250                255

Ser Asn Ser Arg Ser Gln Ile Lys Val Ala Leu Asp Asn Ala Gly Lys
            260                265                270

Ile Met Ser Leu Thr Lys Thr Ala Pro Asp Tyr Leu Val Gly Gln Gln
            275                280                285

Pro Val Glu Asp Ile Ser Ser Asn Arg Ile Tyr Lys Ile Leu Glu Leu
        290                295                300

Asn Gly Tyr Asp Pro Gln Tyr Ala Ala Ser Val Phe Leu Gly Trp Ala
    305                310                315                320

Thr Lys Lys Phe Gly Lys Arg Asn Thr Ile Trp Leu Phe Gly Pro Ala
                325                330                335

Thr Thr Gly Lys Thr Asn Ile Ala Glu Ala Ile Ala His Thr Val Pro
                340                345                350

Phe Tyr Gly Cys Val Asn Trp Thr Asn Glu Asn Phe Pro Phe Asn Asp
            355                360                365

Cys Val Asp Lys Met Val Ile Trp Trp Glu Glu Gly Lys Met Thr Ala
    370                375                380

Lys Val Val Glu Ser Ala Lys Ala Ile Leu Gly Gly Ser Lys Val Arg
385                390                395                400

Val Asp Gln Lys Cys Lys Ser Ser Ala Gln Ile Asp Pro Thr Pro Val
                405                410                415

Ile Val Thr Ser Asn Thr Asn Met Cys Ala Val Ile Asp Gly Asn Ser
                420                425                430

Thr Thr Phe Glu His Gln Gln Pro Leu Gln Asp Arg Met Phe Lys Phe
            435                440                445

Glu Leu Thr Arg Arg Leu Asp His Asp Phe Gly Lys Val Thr Lys Gln
        450                455                460

Glu Val Lys Asp Phe Phe Arg Trp Ala Lys Asp His Val Val Glu Val
465                470                475                480

Glu His Glu Phe Tyr Val Lys Lys Gly Gly Ala Lys Lys Arg Pro Ala
                485                490                495

Pro Ser Asp Ala Asp Ile Ser Glu Pro Lys Arg Val Arg Glu Ser Val
            500                505                510

Ala Gln Pro Ser Thr Ser Asp Ala Glu Ala Ser Ile Asn Tyr Ala Asp
            515                520                525

Arg Tyr Gln Asn Lys Cys Ser Arg His Val Gly Met Asn Leu Met Leu
        530                535                540

Phe Pro Cys Arg Gln Cys Glu Arg Leu Asn Gln Asn Ser Asn Ile Cys
545                550                555                560

Phe Thr His Gly Val Lys Asp Cys Leu Glu Cys Phe Pro Val Ser Glu
                565                570                575

Ser Gln Pro Val Ser Val Val Lys Lys Ala Tyr Gln Lys Leu Cys Tyr
            580                585                590

Ile His His Ile Met Gly Lys Val Pro Asp Ala Cys Thr Ala Cys Asp
            595                600                605

Leu Val Asn Val Asp Leu Asp Asp Cys Val Ser Glu Gln
    610                615                620

<210> SEQ ID NO 7
<211> LENGTH: 1866
<212> TYPE: DNA
<213> ORGANISM: Artificial sequence
```

```
<220> FEATURE:
<223> OTHER INFORMATION: AAV2 rep
<220> FEATURE:
<221> NAME/KEY: CDS
<222> LOCATION: (1)..(1866)

<400> SEQUENCE: 7 atg ccg ggg ttt tac gag att gtg att aag gtc ccc agc gac ctt gac          48
Met Pro Gly Phe Tyr Glu Ile Val Ile Lys Val Pro Ser Asp Leu Asp
1               5                   10                  15 gag cat ctg ccc ggc att tct gac agc ttt gtg aac tgg gtg gcc gag          96
Glu His Leu Pro Gly Ile Ser Asp Ser Phe Val Asn Trp Val Ala Glu
                20                  25                  30 aag gaa tgg gag ttg ccg cca gat tct gac atg gat ctg aat ctg att         144
Lys Glu Trp Glu Leu Pro Pro Asp Ser Asp Met Asp Leu Asn Leu Ile
            35                  40                  45 gag cag gca ccc ctg acc gtg gcc gag aag ctg cag cgc gac ttt ctg         192
Glu Gln Ala Pro Leu Thr Val Ala Glu Lys Leu Gln Arg Asp Phe Leu
        50                  55                  60 acg gaa tgg cgc cgt gtg agt aag gcc ccg gag gct ctt ttc ttt gtg         240
Thr Glu Trp Arg Arg Val Ser Lys Ala Pro Glu Ala Leu Phe Phe Val
65                  70                  75                  80 caa ttt gag aag gga gag agc tac ttc cac atg cac gtg ctc gtg gaa         288
Gln Phe Glu Lys Gly Glu Ser Tyr Phe His Met His Val Leu Val Glu
                85                  90                  95 acc acc ggg gtg aaa tcc atg gtt ttg gga cgt ttc ctg agt cag att         336
Thr Thr Gly Val Lys Ser Met Val Leu Gly Arg Phe Leu Ser Gln Ile
                100                 105                 110 cgc gaa aaa ctg att cag aga att tac cgc ggg atc gag ccg act ttg         384
Arg Glu Lys Leu Ile Gln Arg Ile Tyr Arg Gly Ile Glu Pro Thr Leu
            115                 120                 125 cca aac tgg ttc gcg gtc aca aag acc aga aat ggc gcc gga ggc ggg         432
Pro Asn Trp Phe Ala Val Thr Lys Thr Arg Asn Gly Ala Gly Gly Gly
        130                 135                 140 aac aag gtg gtg gat gag tgc tac atc ccc aat tac ttg ctc ccc aaa         480
Asn Lys Val Val Asp Glu Cys Tyr Ile Pro Asn Tyr Leu Leu Pro Lys
145                 150                 155                 160 acc cag cct gag ctc cag tgg gcg tgg act aat atg gaa cag tat tta         528
Thr Gln Pro Glu Leu Gln Trp Ala Trp Thr Asn Met Glu Gln Tyr Leu
                165                 170                 175 agc gcc tgt ttg aat ctc acg gag cgt aaa cgg ttg gtg gcg cag cat         576
Ser Ala Cys Leu Asn Leu Thr Glu Arg Lys Arg Leu Val Ala Gln His
            180                 185                 190 ctg acg cac gtg tcg cag acg cag gag cag aac aaa gag aat cag aat         624
Leu Thr His Val Ser Gln Thr Gln Glu Gln Asn Lys Glu Asn Gln Asn
        195                 200                 205 ccc aat tct gat gcg ccg gtg atc aga tca aaa act tca gcc agg tac         672
Pro Asn Ser Asp Ala Pro Val Ile Arg Ser Lys Thr Ser Ala Arg Tyr
        210                 215                 220 atg gag ctg gtc ggg tgg ctc gtg gac aag ggg att acc tcg gag aag         720
Met Glu Leu Val Gly Trp Leu Val Asp Lys Gly Ile Thr Ser Glu Lys
225                 230                 235                 240 cag tgg atc cag gag gac cag gcc tca tac atc tcc ttc aat gcg gcc         768
Gln Trp Ile Gln Glu Asp Gln Ala Ser Tyr Ile Ser Phe Asn Ala Ala
                245                 250                 255 tcc aac tcg cgg tcc caa atc aag gct gcc ttg gac aat gcg gga aag         816
Ser Asn Ser Arg Ser Gln Ile Lys Ala Ala Leu Asp Asn Ala Gly Lys
            260                 265                 270 att atg agc ctg act aaa acc gcc ccc gac tac ctg gtg ggc cag cag         864
Ile Met Ser Leu Thr Lys Thr Ala Pro Asp Tyr Leu Val Gly Gln Gln
        275                 280                 285
```

-continued

```
ccc gtg gag gac att tcc agc aat cgg att tat aaa att ttg gaa cta       912
Pro Val Glu Asp Ile Ser Ser Asn Arg Ile Tyr Lys Ile Leu Glu Leu
    290             295             300 aac ggg tac gat ccc caa tat gcg gct tcc gtc ttt ctg gga tgg gcc       960
Asn Gly Tyr Asp Pro Gln Tyr Ala Ala Ser Val Phe Leu Gly Trp Ala
305             310             315             320 acg aaa aag ttc ggc aag agg aac acc atc tgg ctg ttt ggg cct gca      1008
Thr Lys Lys Phe Gly Lys Arg Asn Thr Ile Trp Leu Phe Gly Pro Ala
            325             330             335 act acc ggg aag acc aac atc gcg gag gcc ata gcc cac act gtg ccc      1056
Thr Thr Gly Lys Thr Asn Ile Ala Glu Ala Ile Ala His Thr Val Pro
            340             345             350 ttc tac ggg tgc gta aac tgg acc aat gag aac ttt ccc ttc aac gac      1104
Phe Tyr Gly Cys Val Asn Trp Thr Asn Glu Asn Phe Pro Phe Asn Asp
            355             360             365 tgt gtc gac aag atg gtg atc tgg tgg gag gag ggg aag atg acc gcc      1152
Cys Val Asp Lys Met Val Ile Trp Trp Glu Glu Gly Lys Met Thr Ala
    370             375             380 aag gtc gtg gag tcg gcc aaa gcc att ctc gga gga agc aag gtg cgc      1200
Lys Val Val Glu Ser Ala Lys Ala Ile Leu Gly Gly Ser Lys Val Arg
385             390             395             400 gtg gac cag aaa tgc aag tcc tcg gcc cag ata gac ccg act ccc gtg      1248
Val Asp Gln Lys Cys Lys Ser Ser Ala Gln Ile Asp Pro Thr Pro Val
            405             410             415 atc gtc acc tcc aac acc aac atg tgc gcc gtg att gac ggg aac tca      1296
Ile Val Thr Ser Asn Thr Asn Met Cys Ala Val Ile Asp Gly Asn Ser
            420             425             430 acg acc ttc gaa cac cag cag ccg ttg caa gac cgg atg ttc aaa ttt      1344
Thr Thr Phe Glu His Gln Gln Pro Leu Gln Asp Arg Met Phe Lys Phe
            435             440             445 gaa ctc acc cgc cgt ctg gat cat gac ttt ggg aag gtc acc aag cag      1392
Glu Leu Thr Arg Arg Leu Asp His Asp Phe Gly Lys Val Thr Lys Gln
    450             455             460 gaa gtc aaa gac ttt ttc cgg tgg gca aag gat cac gtg gtt gag gtg      1440
Glu Val Lys Asp Phe Phe Arg Trp Ala Lys Asp His Val Val Glu Val
465             470             475             480 gag cat gaa ttc tac gtc aaa aag ggt gga gcc aag aaa aga ccc gcc      1488
Glu His Glu Phe Tyr Val Lys Lys Gly Gly Ala Lys Lys Arg Pro Ala
            485             490             495 ccc agt gac gca gat ata agt gag ccc aaa cgg gtg cgc gag tca gtt      1536
Pro Ser Asp Ala Asp Ile Ser Glu Pro Lys Arg Val Arg Glu Ser Val
            500             505             510 gcg cag cca tcg acg tca gac gcg gaa gct tcg atc aac tac gca gac      1584
Ala Gln Pro Ser Thr Ser Asp Ala Glu Ala Ser Ile Asn Tyr Ala Asp
            515             520             525 agg tac caa aac aaa tgt tct cgt cac gtg ggc atg aat ctg atg ctg      1632
Arg Tyr Gln Asn Lys Cys Ser Arg His Val Gly Met Asn Leu Met Leu
    530             535             540 ttt ccc tgc aga caa tgc gag aga atg aat cag aat tca aat atc tgc      1680
Phe Pro Cys Arg Gln Cys Glu Arg Met Asn Gln Asn Ser Asn Ile Cys
545             550             555             560 ttc act cac gga cag aaa gac tgt tta gag tgc ttt ccc gtg tca gaa      1728
Phe Thr His Gly Gln Lys Asp Cys Leu Glu Cys Phe Pro Val Ser Glu
            565             570             575 tct caa ccc gtt tct gtc gtc aaa aag gcg tat cag aaa ctg tgc tac      1776
Ser Gln Pro Val Ser Val Val Lys Lys Ala Tyr Gln Lys Leu Cys Tyr
            580             585             590 att cat cat atc atg gga aag gtg cca gac gct tgc act gcc tgc gat      1824
Ile His His Ile Met Gly Lys Val Pro Asp Ala Cys Thr Ala Cys Asp
```

-continued

```
          595                     600                     605
ctg gtc aat gtg gat ttg gat gac tgc atc ttt gaa caa taa          1866
Leu Val Asn Val Asp Leu Asp Asp Cys Ile Phe Glu Gln
    610                     615                     620

<210> SEQ ID NO 8
<211> LENGTH: 621
<212> TYPE: PRT
<213> ORGANISM: Artificial sequence
<220> FEATURE:
<223> OTHER INFORMATION: Synthetic Construct

<400> SEQUENCE: 8

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335
```

-continued

```
Thr Thr Gly Lys Thr Asn Ile Ala Glu Ala Ile Ala His Thr Val Pro
            340             345             350

Phe Tyr Gly Cys Val Asn Trp Thr Asn Glu Asn Phe Pro Phe Asn Asp
            355             360             365

Cys Val Asp Lys Met Val Ile Trp Trp Glu Glu Gly Lys Met Thr Ala
        370             375             380

Lys Val Val Glu Ser Ala Lys Ala Ile Leu Gly Gly Ser Lys Val Arg
385             390             395             400

Val Asp Gln Lys Cys Lys Ser Ser Ala Gln Ile Asp Pro Thr Pro Val
            405             410             415

Ile Val Thr Ser Asn Thr Asn Met Cys Ala Val Ile Asp Gly Asn Ser
            420             425             430

Thr Thr Phe Glu His Gln Gln Pro Leu Gln Asp Arg Met Phe Lys Phe
            435             440             445

Glu Leu Thr Arg Arg Leu Asp His Asp Phe Gly Lys Val Thr Lys Gln
    450             455             460

Glu Val Lys Asp Phe Phe Arg Trp Ala Lys Asp His Val Val Glu Val
465             470             475             480

Glu His Glu Phe Tyr Val Lys Lys Gly Gly Ala Lys Lys Arg Pro Ala
            485             490             495

Pro Ser Asp Ala Asp Ile Ser Glu Pro Lys Arg Val Arg Glu Ser Val
            500             505             510

Ala Gln Pro Ser Thr Ser Asp Ala Glu Ala Ser Ile Asn Tyr Ala Asp
            515             520             525

Arg Tyr Gln Asn Lys Cys Ser Arg His Val Gly Met Asn Leu Met Leu
    530             535             540

Phe Pro Cys Arg Gln Cys Glu Arg Met Asn Gln Asn Ser Asn Ile Cys
545             550             555             560

Phe Thr His Gly Gln Lys Asp Cys Leu Glu Cys Phe Pro Val Ser Glu
            565             570             575

Ser Gln Pro Val Ser Val Val Lys Lys Ala Tyr Gln Lys Leu Cys Tyr
            580             585             590

Ile His His Ile Met Gly Lys Val Pro Asp Ala Cys Thr Ala Cys Asp
    595             600             605

Leu Val Asn Val Asp Leu Asp Asp Cys Ile Phe Glu Gln
    610             615             620

<210> SEQ ID NO 9
<211> LENGTH: 16
<212> TYPE: DNA
<213> ORGANISM: Artificial sequence
<220> FEATURE:
<223> OTHER INFORMATION: spacer sequence

<400> SEQUENCE: 9
atgatttaaa tcaggt                                                        16
```